United States Patent [19]
Allaway et al.

[11] Patent Number: 6,107,019
[45] Date of Patent: Aug. 22, 2000

[54] METHOD FOR PREVENTING HIV-1 INFECTION OF CD4+ CELLS

[75] Inventors: Graham P. Allaway, Mohegan Lake; Virginia M. Litwin, Fayetteville; Paul J. Maddon, Elmsford; William C. Olson, Ossining, all of N.Y.

[73] Assignee: Progenics Pharmaceuticals, Inc., Tarrytown, N.Y.

[21] Appl. No.: 08/876,078

[22] Filed: Jun. 13, 1997

Related U.S. Application Data

[63] Continuation-in-part of application No. 08/831,823, Apr. 2, 1997.
[60] Provisional application No. 60/019,715, Jun. 14, 1996, and provisional application No. 60/014,532, Apr. 2, 1996.
[51] Int. Cl.$^7$ ..................................................... C12Q 1/70
[52] U.S. Cl. .............................. 435/5; 435/7.2; 435/7.21; 435/7.24; 435/7.92; 435/7.93; 436/537; 436/542
[58] Field of Search ................................ 435/5, 7.2, 7.21, 435/7.24, 7.92, 7.93; 436/537, 542

[56] References Cited

PUBLICATIONS

Fahey et al., *Clin Exp Immunol.* 88:1–5, 1992.
Fox, J.L., *Bio/Technology* 12:128, Feb. 1994.
Haynes et al., *Ann. Med.* 28:39–41, 1996.
Feng et al., *Science* 272:872–877, May 10, 1996.
Deng et al., *Nature* 381:661–666, Jun. 20, 1996.
Oellerich et al., J. Clin. Chem. Clin. Biochem. 22:895–904, 1984.
Alkhatib, Ghalb, et al., "CC CKR5: A RANTES, MIP–1α, MIP–1β Receptor as a Fusion Cofactor for Macrophage–Tropic HIV–1" *Science* (Jun. 28, 1996) vol. 272:1955–1958 (Exhibit 1).
Arenzana–Selsdedos, Fernando, et al., "HIV blocked by chemokine antagonist" *Nature* (Oct. 3, 1996) vol. 383:400 (Exhibit 2).
Bleul, Conrad, C., et al., "The lymphocyte chemoattractant SDF–1 is a ligand for LESTR/fusion and blocks HIV–1 entry" *Nature* (Aug. 29, 1996) vol. 382:829–832 (Exhibit 3).
Choe, Hyeryun, et al., "The β–Chemokine Receptors CCR3 and CCR5 Facilitate Infection by Primary HIV–1 Isolates" *Cell* (Jun. 28, 1996) vol. 85:1135–1148 (Exhibit 4).
Cocchi, Florenza, et al., "Identification Of RANTES, MIP–1α, and MIP–1β as the Major HIV–Suppressive Factors Produced by CD8+ T Cells" *Science* (Dec. 15, 1995) vol. 270: 1811–1815 (Exhibit 5).
Dragic, Tatjana, et al., "HIV–1 entry into CD4+ cells is mediated by the chemokine receptor CC–CKR–5" *Nature* (Jun. 20, 1996) vol. 381:667–673 (Exhibit 6).
Gong, Jiang–Hong, et al., "Antagonists Of Monocyte Chemoattractant Protein 1 Identified By Modification Of Functionally Critical $NH_2$–terminal Residues" *J. Exp. Med.* (Feb. 1995) vol. 181:631–640 (Exhibit 7).

Gong, Jian–Hong, et al., "RANTES and MCP–3 Antagonists Bind Multiple Chemokine Receptors" *The Journal of Biological Chemistry* (May 1996) vol. 371:10521–10527 (Exhibit 8).
Jones, Simon, A., et al., "Chemokine Antagonists That Discriminate between Interleukin–8 Receptors" *The Journal of Biological Chemistry* (Jun. 27, 1997) vol. 272:16166–16169. (Exhibit 9).
McKnight, Aine, et al., "Inhibition of Human Immunodeficiency Virus Fusion by a Monoclonal Antibody to a Coreceptor (CXCR4) Is both Cell Type and Virus Strain Dependent" *Journal of Virology* (Feb. 1997) vol. 71: No. 2 pp. 1692–1696 (Exhibit 10).
Moser, Bernhard, et al., "Interleukin–8 Antagonists Generated by N–terminal Modification" *The Journal of Biological Chemistry* (Apr. 1993) vol. 268:7125–7128 (Exhibit 11).
Oberlin, Estelle, et al., "The CXC chemokine SDF–1 is the ligand for LESTR/fusion and prevents infection by T–cell–line–adapted HIV–1" *Nature* (Aug. 29, 1996) vol. 382:833–835 (Exhibit 12).
Raport, Carol, J., et al., "New members of the chemokine receptor gene family" *Journal of Leukocyte Biology* (Jan. 1996) vol. 59:18–23 ; (Exhibit 13).
Simmons, Graham, et al., "Potent Inhibition of HIV–1 Infectivity in Macrophages and Lymphocytes by a Novel CCR5 Antagonist" *Science* (Apr. 11, 1997) vol. 276:276–279 (Exhibit 14).

(List continued on next page.)

*Primary Examiner*—Robert D. Budens
*Attorney, Agent, or Firm*—John P. White; Cooper & Dunham LLP

[57] ABSTRACT

This invention provides methods for inhibiting fusion of HIV-1 to CD4+ cells which comprise contacting CD4+ cells with a non-chemokine agent capable of binding to a chemokine receptor in an amount and under conditions such that fusion of HIV-1 to the CD4+ cells is inhibited. This invention also provides methods for inhibiting HIV-1 infection of CD4+ cells which comprise contacting CD4+ cells with a non-chemokine agent capable of binding to a chemokine receptor in an amount and under conditions such that fusion of HIV-1 to the CD4+ cells is inhibited, thereby inhibiting the HIV-1 infection. This invention provides non-chemokine agents capable of binding to the chemokine receptor and inhibiting fusion of HIV-1 to CD4+ cells. This invention also provides pharmaceutical compositions comprising an amount of the non-chemokine agent capable of binding to the chemokine receptor and inhibiting fusion of HIV-1 to CD4+ cells effective to prevent fusion of HIV-1 to CD4+ cells and a pharmaceutically acceptable carrier.

12 Claims, 8 Drawing Sheets

OTHER PUBLICATIONS

Trkola, Alexandra, et al., "CD4–dependent, antibody–sensitive interactions between HIV–1 and its co–receptor CCR–5" *Nature* (Nov. 14, 1996) vol. 384:184–187 (Exhibit 15).

Wells, Timothy, N.C., et al., "Selectivity and antagonism of chemokine receptors" *Journal of Leukocyte Biology* (Jan. 1996) vol. 59:53–60 (Exhibit 16).

Wu, Lijun, et al., "CCR5 Levels and Expression Pattern Correlate with Infectability by Macrophage–tropic HIV–1, In Vitro" *J. Exp. Med.* (May 5, 1997) vol. 185:1681–1691 (Exhibit 18).

Zhang, Y,J., et al., "Structure/Activity Analysis of Human Monocyte Chemoattractant Protein–1 (MCP–1) by Mutagenesis" *The Journal of Biological Chemistry* (Jun. 1994) vol. 269: 15918–15924 (Exhibit 19).

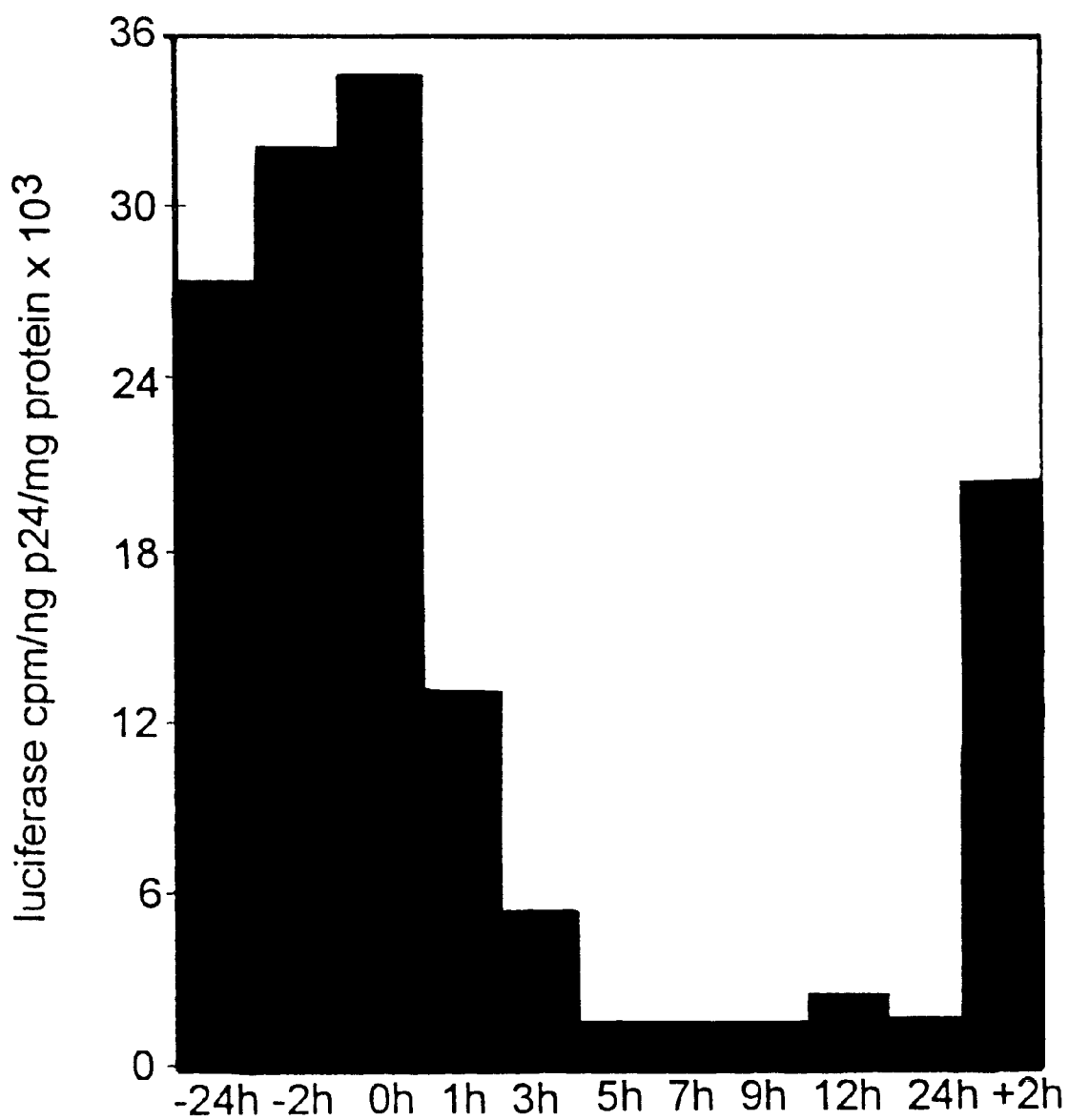

METHOD FOR PREVENTING HIV-1 INFECTION OF CD4+ CELLS

This application is a continuation-in-part of U.S. Ser. No. 08/831,823, filed Apr. 2, 1997, which claims priority of U.S. Provisional Application No. 60/019,715, filed Jun. 14, 1996, now abandoned, and U.S. Provisional Application No. 60/014,532, filed Apr. 2, 1996, now abandoned. The contents of the applications being referred to above are incorporated by reference into this application.

Throughout this application, various references are referred to within parentheses. Disclosures of these publications in their entireties are hereby incorporated by reference into this application to more fully describe the state of the art to which this invention pertains. Full bibliographic citation for these references may be found at the end of each series of experiments.

BACKGROUND OF THE INVENTION

Chemokines are a family of related soluble proteins of molecular weight between 8 and 10 KDa, secreted by lymphocytes and other cells, which bind receptors on target cell surfaces resulting in the activation and mobilization of leukocytes, for example in the inflammatory process. Recently, Cocchi et al. demonstrated that the chemokines RANTES, MIP-1α and MIP-1β are factors produced by CD8+ T lymphocytes which inhibit infection by macrophage-tropic primary isolates of HIV-1, but not infection by laboratory-adapted strains of the virus (1). These chemokines are members of the C—C group of chemokines, so named because they have adjacent cysteine residues, unlike the C-X-C group which has a single amino acid separating these residues (2). While Cocchi et al. found that expression of HIV-1 RNA was suppressed by treatment with the chemokines, they did not identify the site of action of these molecules.

A resonance energy transfer (RET) assay of HIV-1 envelope glycoprotein-mediated membrane fusion was used to determine whether fusion mediated by the envelope glycoprotein from the primary macrophage-tropic isolate of HIV-$1_{JR\text{-}FL}$ would be specifically inhibited by chemokines, when compared with fusion mediated by the envelope glycoprotein from the laboratory-adapted T lymphotropic strain HIV-$1_{LAI}$. As described below, it was demonstrated that this is indeed the case. This demonstrates that some chemokine receptors are fusion accessory molecules required for HIV-1 infection. Previous studies have indicated that unidentified cell surface molecules are required for virus entry in addition to the HIV-1 receptor, CD4. While CD4 is required for HIV-1 attachment, the accessory molecules are required for the membrane fusion step of entry. These accessory molecules are generally expressed only on human cells, so HIV-1 does not infect non-human CD4+ cells (3–6). Moreover it is possible to complement non-human CD4+ cells by fusing them (using polyethylene glycol) with CD4− human cells, resulting in a heterokaryon which is a competent target for HIV-1 envelope-mediated membrane fusion (7,8). These studies have been performed using laboratory-adapted T lymphotropic strains of the virus.

In some cases, it appears that fusion accessory molecules are found on a subset of human CD4+ cells and are required for infection by HIV-1 isolates with particular tropisms. For example, macrophage-tropic primary strains of HIV-1 such as HIV-$1_{JR\text{-}FL}$ may have different requirements for accessory molecules compared with laboratory-adapted T lymphotropic strains such as HIV-$1_{LAI}$. This phenomenon may explain differences in tropism between HIV-1 strains.

The current invention comprises a series of new therapeutics for HIV-1 infection. It was demonstrated for the first time that chemokines act at the fusion step of HIV-1 entry and specifically inhibit membrane fusion mediated by the envelope glycoprotein of primary macrophage-tropic primary viral isolates, not laboratory-adapted T lymphotrophic strains of the virus. Primary macrophage-tropic isolates of the virus are of particular importance since they are the strains usually involved in virus transmission, and may have particular importance in the pathogenesis of HIV-1 infection.

These results were obtained using a resonance energy transfer (RET) assay of HIV-1 envelope-mediated membrane fusion. Moreover, this assay is used to identify non-chemokines, including fragments of chemokines and modified chemokines, that inhibit HIV-1 envelope glycoprotein-mediated membrane fusion and thereby neutralize the virus, yet do not induce an inflammatory response.

SUMMARY OF THE INVENTION

This invention provides a method for inhibiting fusion of HIV-1 to CD4+ cells which comprises contacting CD4+ cells with a non-chemokine agent capable of binding to a chemokine receptor in an amount and under conditions such that fusion of HIV-1 to the CD4+ cells is inhibited.

This invention also provides a method for inhibiting HIV-1 infection of CD4+ cells which comprises contacting CD4+ cells with a non-chemokine agent capable of binding to a chemokine receptor in an amount and under conditions such that fusion of HIV-1 to the CD4+ cells is inhibited, thereby inhibiting the HIV-1 infection.

This invention further provides non-chemokine agents capable of binding to the chemokine receptor and inhibiting fusion of HIV-1 to CD4+ cells.

This invention provides an agent which is capable of binding to fusin and inhibiting infection. In an embodiment, the agent is an oligopeptide. In another embodiment, the agent is an polypeptide. In still another embodiment, the agent is an antibody or a portion of an antibody. In a separate embodiment, the agent is a nonypeptidyl agent.

In addition, this invention provides pharmaceutical compositions comprising an amount of the above non-chemokine agents or agents capable of binding to fusin effective to inhibit fusion of HIV-1 to CD4+ cells and a pharmaceutically acceptable carrier.

This invention provides a composition of matter capable of binding to the chemokine receptor and inhibiting fusion of HIV-1 to CD4+ cells comprising a non-chemokine agent linked to a ligand capable of binding to a cell surface receptor of the CD4+ cells other than the chemokine receptor such that the binding of the non-chemokine agent to the chemokine receptor does not prevent the binding of the ligand to the other receptor.

This invention also provides a pharmaceutical composition comprising an amount of the above-described composition of matter effective to inhibit fusion of HIV-1 to CD4+ cells and a pharmaceutically acceptable carrier.

This invention provides a composition of matter capable of binding to the chemokine receptor and inhibiting fusion of HIV-1 to CD4+ cells comprising a non-chemokine agent linked to a compound capable of increasing the in vivo half-life of the non-chemokine agent.

This invention also provides a pharmaceutical composition comprising an amount of a composition of matter comprising a non-chemokine agent linked to a compound capable of increasing the in vivo half-life of the non-chemokine agent effective to inhibit fusion of HIV-1 to CD4+ cells and a pharmaceutically acceptable carrier.

This invention provide methods for reducing the likelihood of HIV-1 infection in a subject comprising administering an above-described pharmaceutical composition to the subject. This invention also provides methods for treating HIV-1 infection in a subject comprising administering an above-described pharmaceutical composition to the subject.

This invention also provides methods for determining whether a non-chemokine agent is capable of inhibiting the fusion of HIV-1 to a CD4+ cell which comprise: (a) contacting (i) a CD4+ cell which is labeled with a first dye and (ii) a cell expressing the HIV-1 envelope glycoprotein on its surface which is labeled with a second dye, in the presence of an excess of the agent under conditions permitting the fusion of the CD4+ cell to the cell expressing the HIV-1 envelope glycoprotein on its surface in the absence of the agent, the first and second dyes being selected so as to allow resonance energy transfer between the dyes; (b) exposing the product of step (a) to conditions which would result in resonance energy transfer if fusion has occurred; and (c) determining whether there is a reduction of resonance energy transfer, when compared with the resonance energy transfer in the absence of the agent, a decrease in transfer indicating that the agent is capable of inhibiting fusion of HIV-1 to CD4+ cells.

% RET resulting from the fusion of PM1 cells and HeLa-env$_{JR-FL}$ (■) or HeLa-env$_{LAI}$ (♦) was measured in the presence and absence of recombinant human chemokines at a range of concentrations: RANTES (80–2.5 ng/ml), MIP-1α (400–12.5 ng/ml) and MIP-1β (200–6.25 ng/ml), as indicated. Chemokines were added simultaneously with the cells at the initiation of a four hour incubation. Data are representative of more than three independent experiments which were run in duplicate. The percent inhibition of RET is defined as follows:

% Inhibition=100 ·[(Max RET–Min RET)–(Exp RET–Min RET)](Max RET–Min RET)

where Max RET is the % RET value obtained at four hours with HeLa-env cells and CD4-expressing cells in the absence of an inhibitory compound; Exp RET is the FRET value obtained for the same cell combination in the presence of an inhibitory compound and Min RET is the background % RET value obtained using HeLa cells in place of HeLa envelope-expressing cells.

Figure 2A:
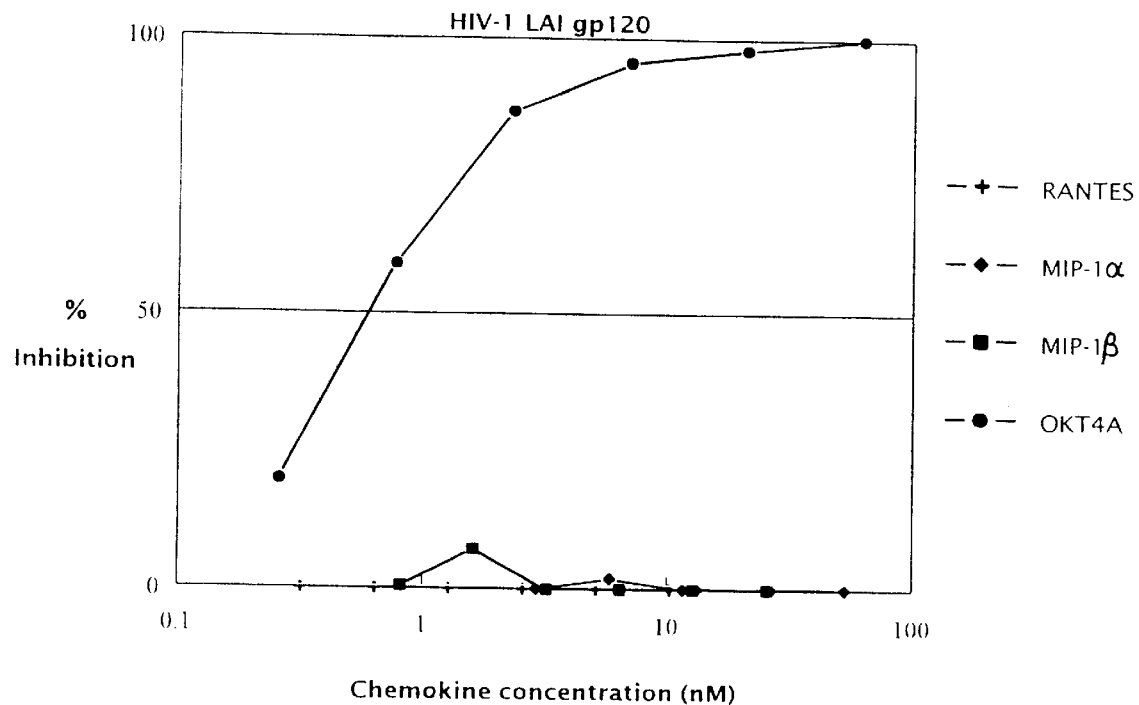
Figure 2B:
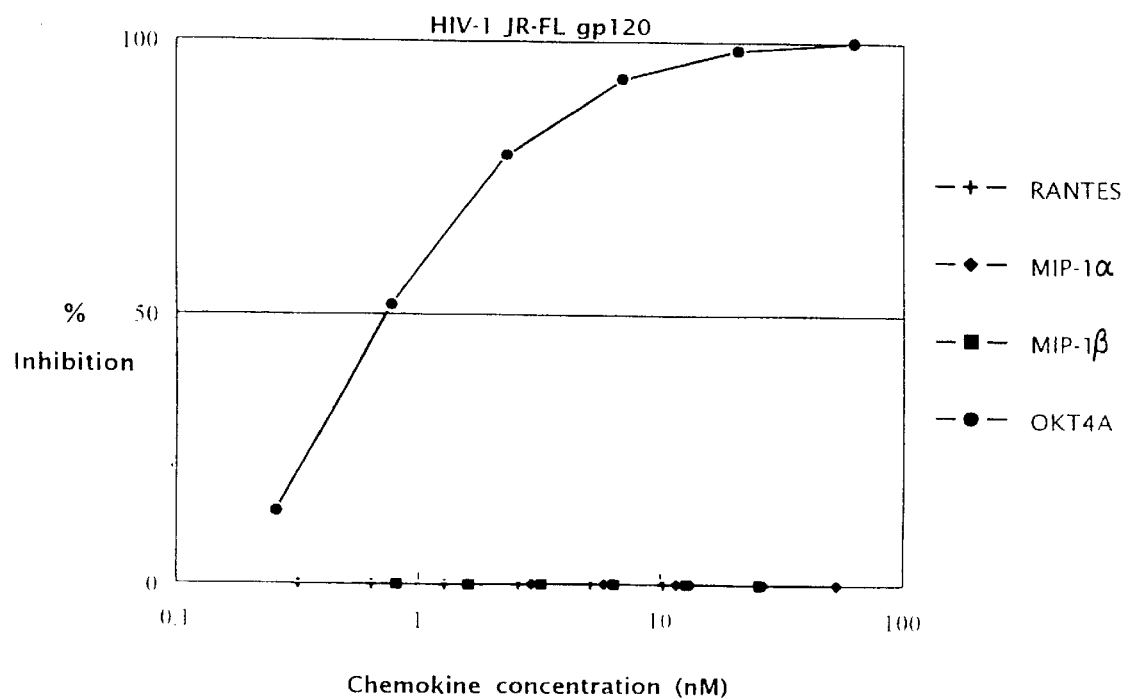

FIG. 2A–B. CD4:HIV-1 gp120 binding in the presence of human chemokines.

Figure 1A:
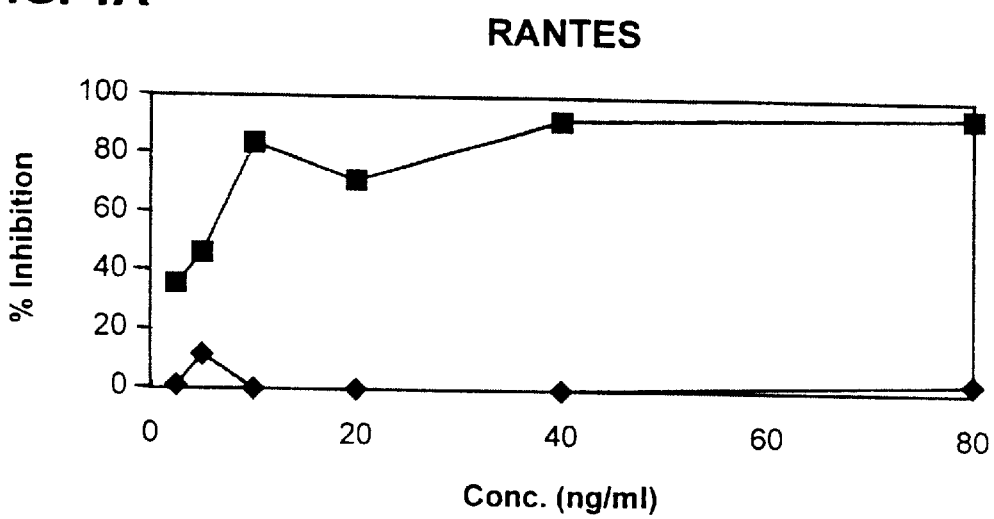
FIGS. 1A–C. Membrane fusion mediated by the HIV-1$_{JR-FL}$ envelope glycoprotein is inhibited by RANTES, MIP-1α and MIP-1β.
Figure 1B:
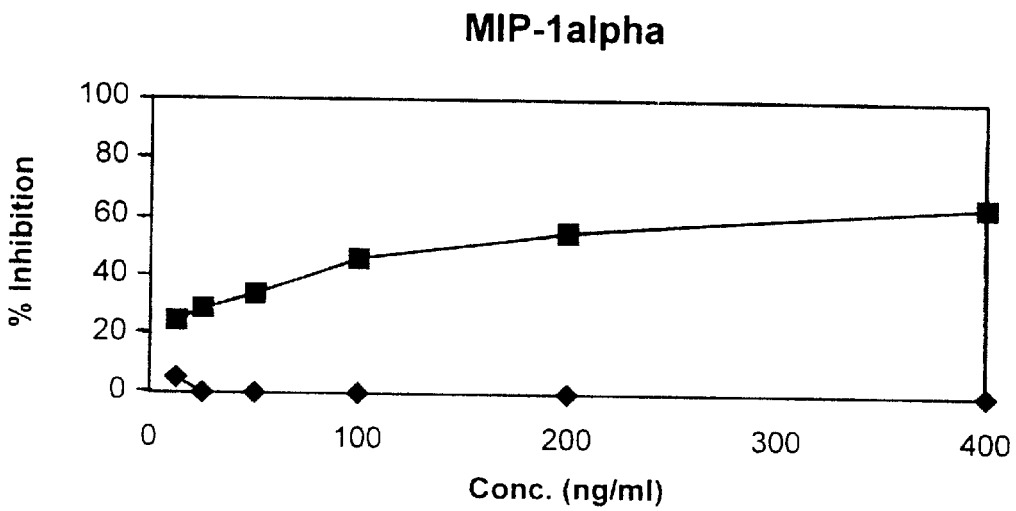
Figure 1C:
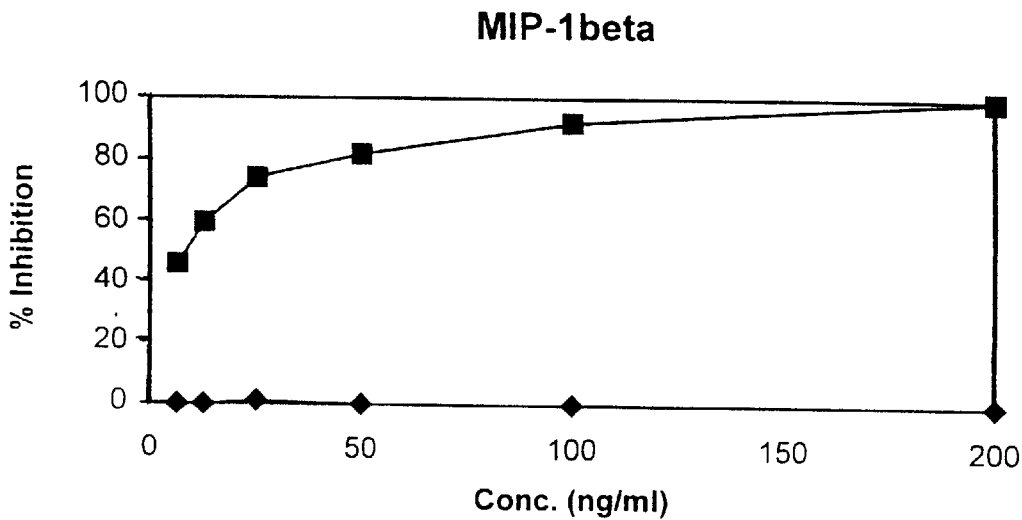

The binding of soluble human CD4 to HIV-1$_{LAI}$ and HIV-1$_{JR-FL}$ gp120 was determined in an ELISA assay in the presence and absence of the monoclonal antibody OKT4A or recombinant human chemokines at a range of concentrations, identical to those used in the RET inhibition studies of FIG. 1: OKT4A (62–0.3 nM), RANTES (10.3–0.3 nM), MIP-1α (53.3–2.9 nM), and MIP-1β (25.6–0.8 nM). Inhibitors were added simultaneously with biotinylated HIV-1 gp120 to soluble CD4 coated microtiter plates (Dynatech Laboratories, Inc., Chantilly, Va.). Following a two hour incubation at room temperature and extensive washing, an incubation with streptavidin-horseradish peroxidase was performed for one hour at room temperature. Following additional washes, substrate was added and the OD at 492 nm determined in an ELISA plate reader. Data are representative of two independent experiments which were run in quadruplicate.

Figure 3B:
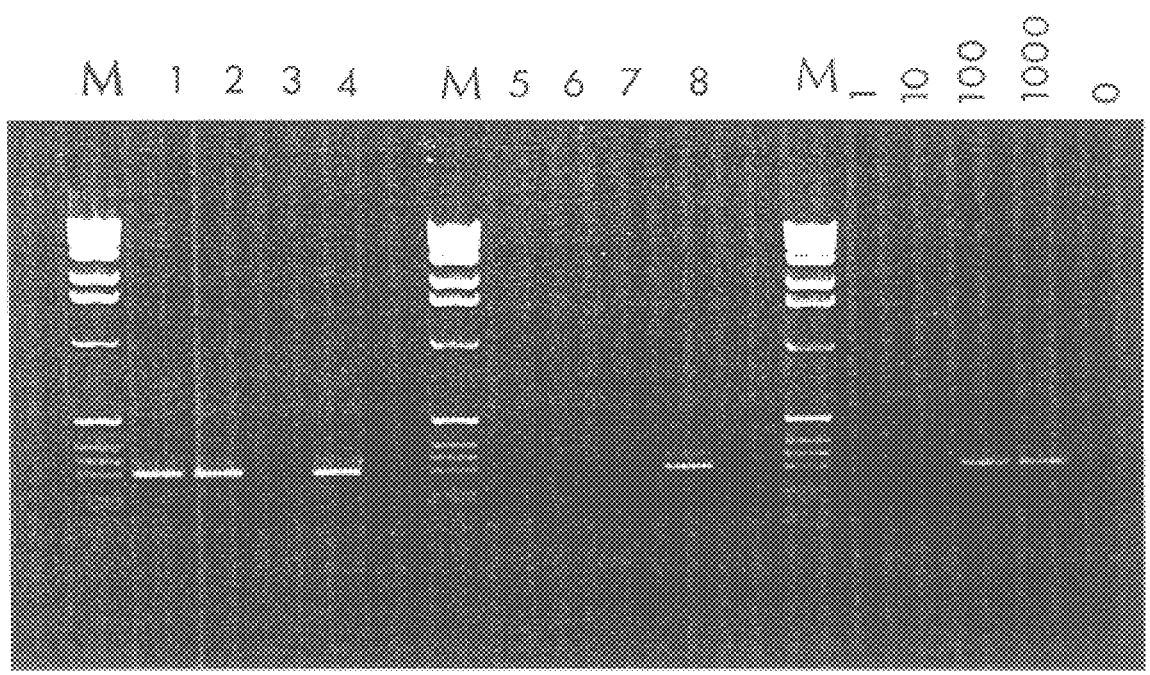

FIG. 3A–B. Specificity. time course and stage of β-chemokine inhibition of HIV-1 replication.

(a) PM1 cells (1×10$^6$) were preincubated with RANTES+MIP-1α+MIP-1β (R/Mα/Mβ; 100 ng/ml of each) for 24 h (−24 h) or 2 h (−2 h), then washed twice with phosphate buffered saline (PBS). HIV-1 (BaL env-complemented) virus (50 ng of p24; see legend to Table 1) was added for 2 h, then the cells were washed and incubated for 48 h before measurement of luciferase activity in cell lysates as described previously (10,11). Alternatively, virus and R/Mα/Mβ were added simultaneously to cells, and at the indicated time points (1 h, 3 h, etc) the cells were washed twice in PBS, resuspended in culture medium and incubated for 48 h prior to luciferase assay. Time 0 represents the positive control, to which no β-chemokines were added. +2 h represents the mixture of virus with cells for 2 h prior to washing twice in PBS, addition of R/Mα/Mβ and continuation of the culture for a further 48 h before luciferase assay.

(b) PM1 cells (1×10$^6$) were infected with HIV-1 (500 pg p24) grown in CEM cells (NL4/3; lanes 1–4) or macrophages (ADA; lanes 5–8), in the presence of 500 ng/ml of RANTES (lanes 1 and 5) or MIP-1β (lanes 2 and 6), or with no β-chemokine (lanes 4 and 8). Lanes 3 and 7 are negative controls (no virus). All viral stocks used for the PCR assay were treated with DNAse for 30 min at 37° C., and tested for DNA contamination before use. After 2 h, the cells were washed and resuspended in medium containing the same β-chemokines for a further 8 h. DNA was then extracted from infected cells using a DNA/RNA isolation kit (US Biochemicals). First round nested PCR was performed with primers: U3+, 5'-CAAGGCTACTTCCCTGATTGGCAGAACTACACA-CCAGG-3'(SEQ ID NO:1) preGag, 5'-AGCAAGCCGAGTCCTGCGTCGAGAG-3' (SEQ ID NO:2) and the second round with primers: LTR-test, 5'-GGGACTTTCCGCTGGGGACTTTC 3' (SEQ ID NO :3) LRC2, 5'-CCTGTTCGGGCGCCACTGCTAGAGATTTTCCAC 3' (SEQ ID NO:4) in a Perkin Elmer 2400 cycler with the following amplification cycles: 94° C. for 5 min, 35 cycles of 94° C. for 30s, 55° C. for 30s, 72° C. for 30s, 72° C. for 7 min. M indicates 1 kb DNA ladder; 1, 10, 100, 1000 indicate number of reference plasmid (pAD8) copies. The assay can detect 100 copies of reverse transcripts.

Figure 4:
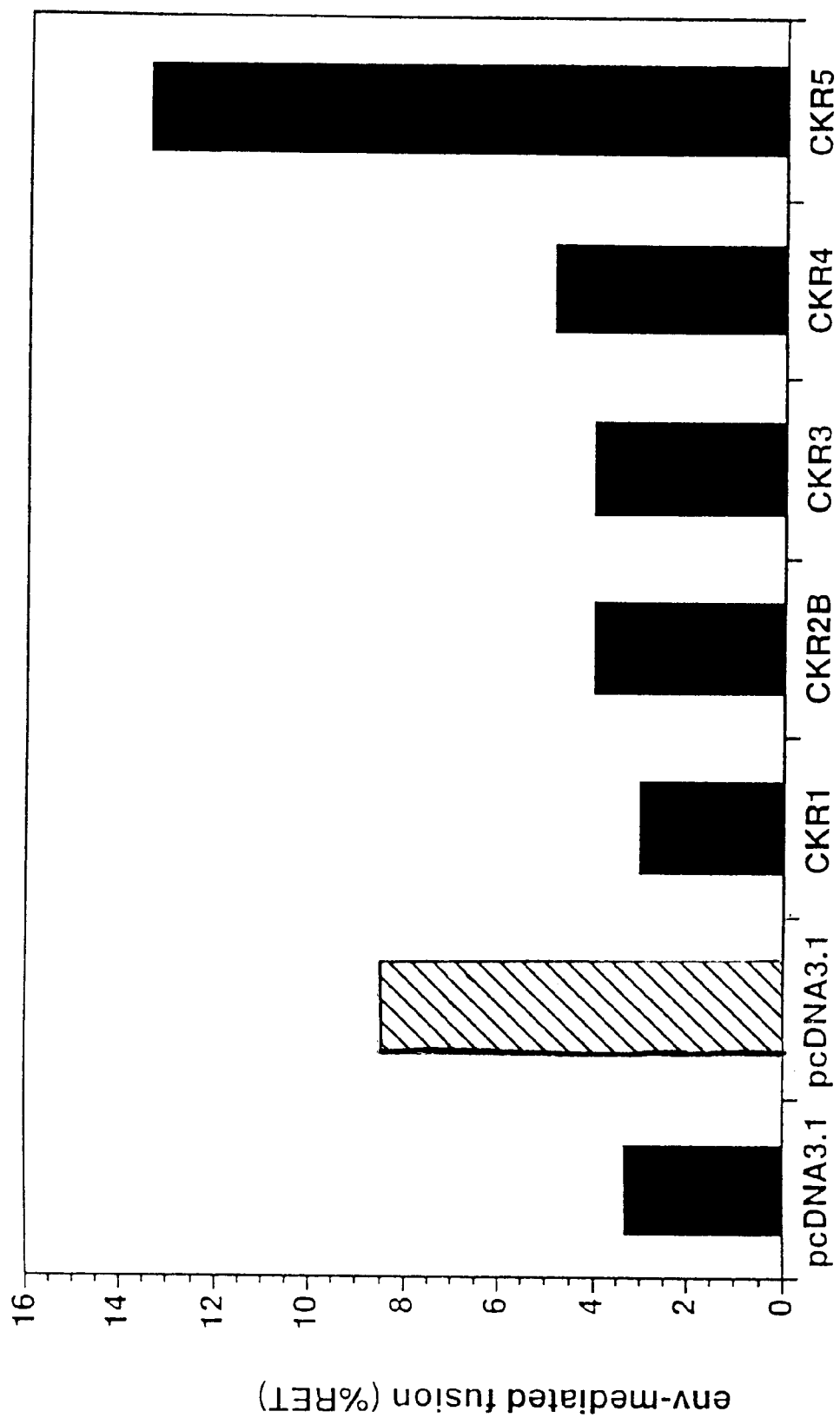

FIG. 4: HIV-1 env-mediated membrane fusion of cells transiently expressing C—C CKR-5.

Membrane fusion mediated by β-chemokine receptors expressed in HeLa cells was demonstrated as follows: Cells were transfected with control plasmid pcDNA3.1 or plasmid pcDNA3.1-CKR constructs using lipofectin (Gibco BRL). The pcDNA3.1 plasmid carries a T7-polymerase promoter and transient expression of β-chemokine receptors was boosted by infecting cells with 1×10$^7$ pfu of vaccinia encoding the T7-polymerase (vFT7.3) 4 h post-lipofection (9). Cells were then cultured overnight in R18-containing media and were tested for their ability to fuse with HeLa-JR-FL cells (filled columns) or HeLa-BRU cells (hatched column) in the RET assay. The FRET with control HeLa cells was between 3% and 4% irrespective of the transfected plasmid.

Figure 5:
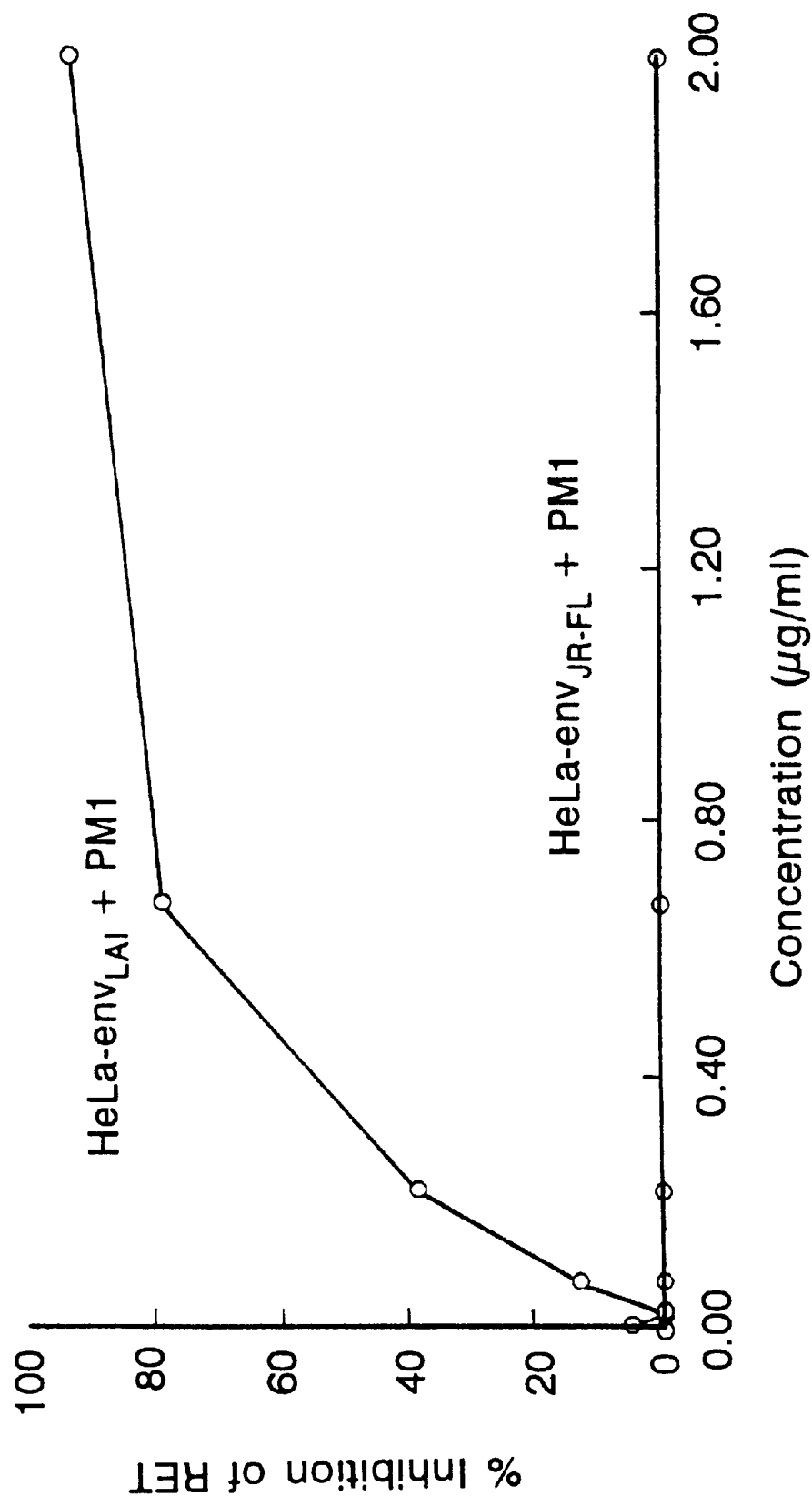

FIG. 5 Membrane fusion mediated by the HIV$_{LAI}$ envelope glycoprotein is inhibited by SDF-1.

% RET resulting from the fusion of PM1 cells and HeLa-env$_{JR-FL}$ or HeLa-env$_{LAI}$ cells (as indicated on the graph) was measured in the presence of recombinant SDF-1α (Gryphon Science, San Francisco) at the indicated concentrations. Experimental method as described in the legend to FIG. 1.

Figure 6B:
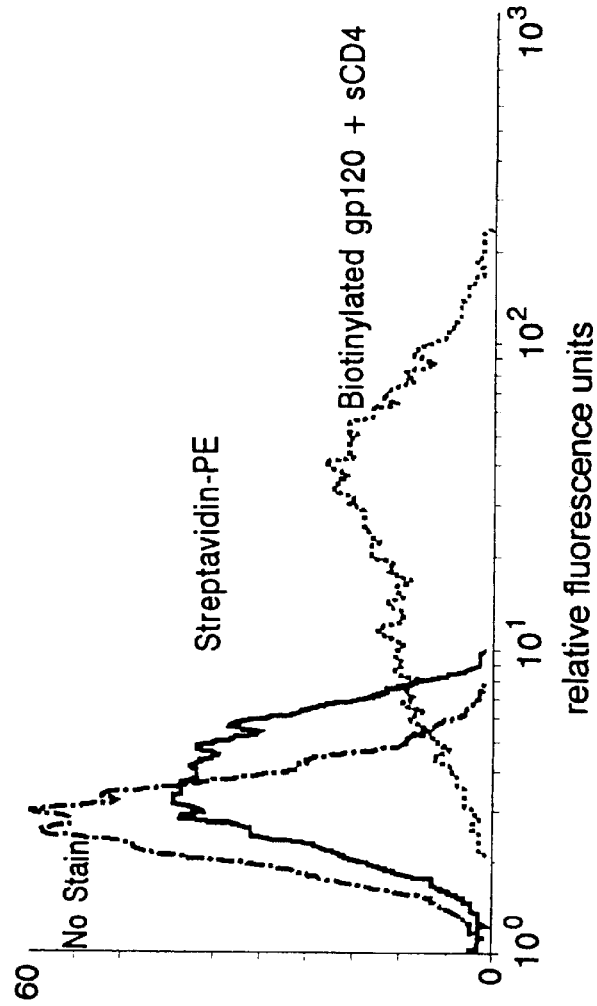
Figure 6A:
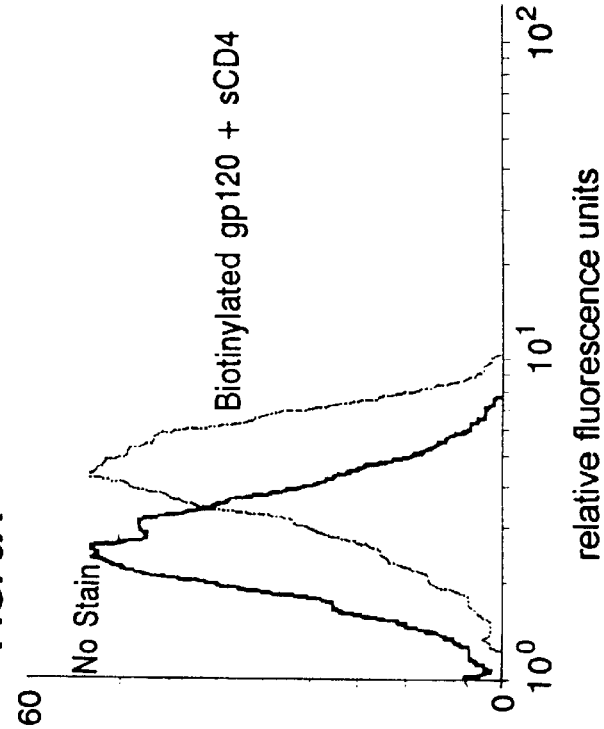

FIGS. 6A–B. Flow cytometric analysis of the binding of sCD4-gp120 complexes to (a)CCR5⁻ and (b)CCR5⁺ L1.2 cells, a murine pre-B lymphoma line. Cells are incubated for 15 min. with equimolar (~100 nM) mixtures of sCD4 and biotinylated HIV-1$_{JR-FL}$ gp120 and then stained with a streptavidin-phycoerythrin conjugate, fixed with 2% paraformaldehyde, and analyzed by FACS. Cell number is plotted on the y-axis.

Figure 7:
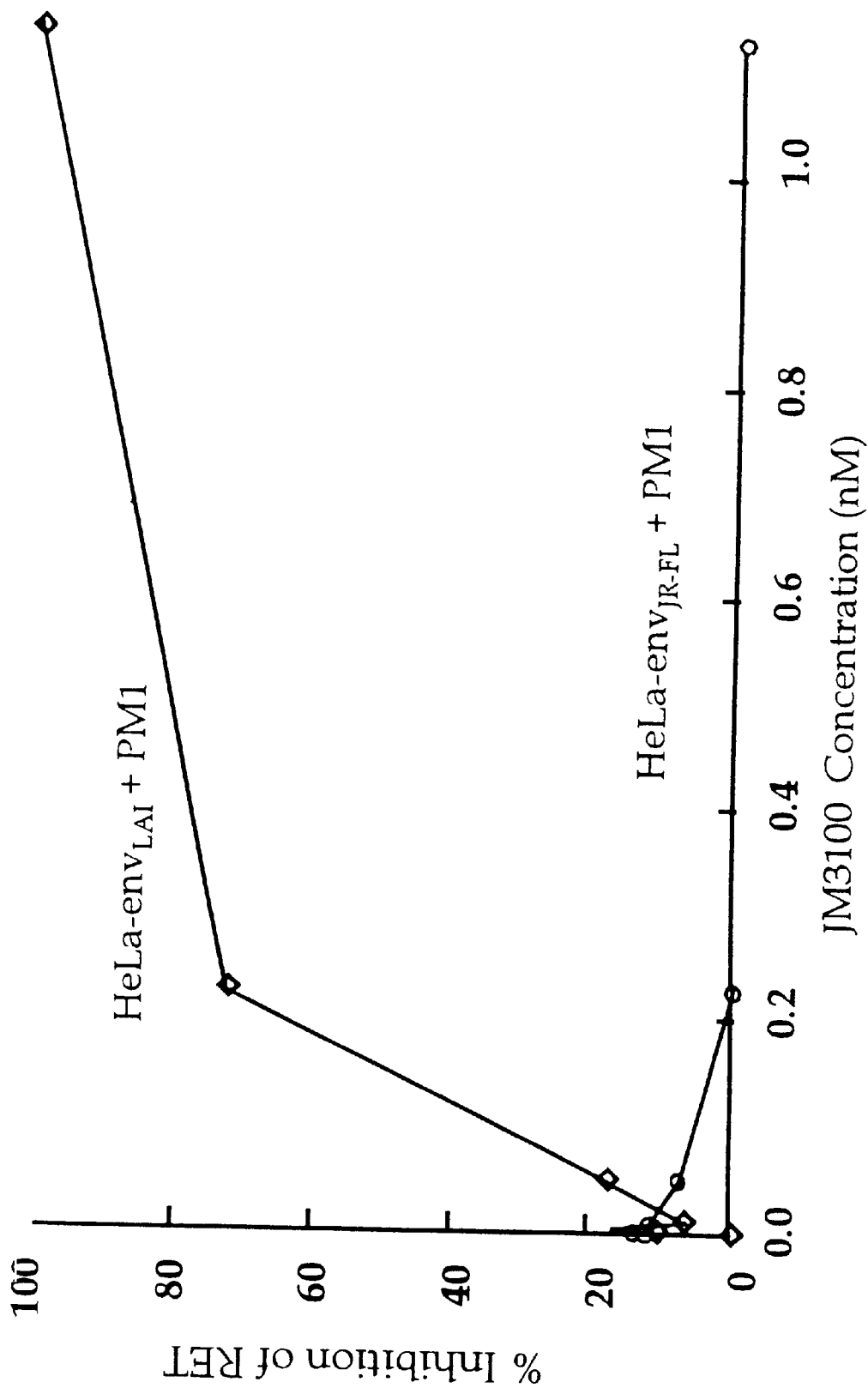

FIG. 7. Inhibition of HIV-1 envelope-mediated cell fusion by the bicyclam JM3100, measured using the RET assay, with the cell combinations indicated.

DETAILED DESCRIPTION OF THE INVENTION

This invention provides a method for inhibiting fusion of HIV-1 to CD4⁺ cells which comprises contacting CD4⁺ cells with a non-chemokine agent capable of binding to a chemokine receptor in an amount and under conditions such that fusion of HIV-1 to the CD4⁺ cells is inhibited.

This invention also provides a method for inhibiting HIV-1 infection of CD4⁺ cells which comprises contacting CD4⁺ cells with a non-chemokine agent capable of binding to a chemokine receptor in an amount and under conditions such that fusion of HIV-1 to the CD4⁺ cells is inhibited, thereby inhibiting the HIV-1 infection.

In this invention, a chemokine means RANTES, MIP-1-α, MIP-1-β or another chemokine which blocks HIV-1 infection. A chemokine receptor means a receptor capable of binding RANTES, MIP-1-α, MIP-1-β or another chemokine which blocks HIV-1 infection. Such chemokine receptor includes but not limited to CCR5, CXCR4, CCR3 and CCR-2b.

Throughout this application, the receptor "fusin" is also named CXCR4 and the chemokine receptor C—C CKR5 is also named CCR5.

The HIV-1 used in this application unless specified will mean clinical or primary or field isolates or HIV-1 viruses which maintain their clinical characteristics. The HIV-1 clinical isolates may be passaged in primary peripheral blood mononuclear cells. The HIV-1 clinical isolates may be macrophage-trophic.

The non-chemokine agents of this invention are capable of binding to chemokine receptors and inhibiting fusion of HIV-1 to CD4⁺ cells. The non-chemokine agents include, but are not limited to, chemokine fragments and chemokine derivatives and analogues, but do not include naturally occurring chemokines. The non-chemokine agents include multimeric forms of the chemokine fragments and chemokine derivatives and analogues or fusion molecules which contain chemokine fragments, derivatives and analogues linked to other molecules.

The non-chemokine agents do not include bicyclams and their derivatives as described in U.S. Pat. No. 5,021,409, issued Jun. 4, 1991, the content of which is incorporated by reference into this application. Some bicyclam derivatives have been previously described with antiviral activities (15, 16).

In an embodiment of this invention, the non-chemokine agent is an oligopeptide. In another embodiment, the non-chemokine agent is a polypeptide. In still another embodiment, the non-chemokine agent is an antibody or a portion thereof. Antibodies against the chemokine receptor may easily be generated by routine experiments. It is also within the level of ordinary skill to synthesize fragments of the antibody capable of binding to the chemokine receptor. In a further embodiment, the non-chemokine agent is a nonpeptidyl agent.

Non-chemokine agents which are purely peptidyl in composition can be either chemically synthesized by solid-phase methods (Merrifield, 1966) or produced using recombinant technology in either prokaryotic or eukaryotic systems. The synthetic and recombinant methods are well known in the art.

Non-chemokine agents which contain biotin or other nonpeptidyl groups can be prepared by chemical modification of synthetic or recombinant chemokines or non-chemokine agents. One chemical modification method involves periodate oxidation of the 2-amino alcohol present on chemokines or non-chemokine agents possessing serine or threonine as their N-terminal amino acid (Geophegan and Stroh, 1992). The resulting aldehyde group can be used to link peptidyl or non-peptidyl groups to the oxidized chemokine or non-chemokine agent by reductive amination, hydrazine, or other chemistries well known to those skilled in the art.

As used herein, a N-terminus of a protein should mean the terminus of the protein after it has been processed. In case of a secretory protein which contains a cleavable signal sequence, the N-terminus of a secretory protein should be the terminus after the cleavage of a signal peptide.

This invention provides a method of identifying these non-chemokine agents. One way of identifying such agents, including non-peptidyl agents, that bind to a chemokine receptor and inhibit fusion of HIV-1 to CD4⁺ cells is to use the following assay: 1) Incubate soluble CD4 with biotinylated gp120 from HIV-1$_{JR-FL}$ or HIV-1$_{LAI}$; 2) Incubate this complex with CCR5 or CXCR4-expressing cells (for HIV-1$_{JR-FL}$ or HIV-1$_{LAI}$ gp120s, respectively) that do not express CD4, in the presence of absence of a candidate inhibitor; 3) Wash and then incubate with streptavidin-phycoerythrin; and 4) Wash and then measure the amount of bound gp120 using a flow cytometer or fluorometer and calculate the degree of inhibition of binding by the inhibitor.

Alternative methods to detect bound gp120 can also be used in place of the biotinylated gp120-streptavidin-phycoerythrin method described above. For example, peroxidase-conjugated gp120 could be used in place of the biotinylated gp120 and binding detected using an appropriate colorimetric substrate for peroxidase, with a spectrometric readout.

This invention further provides the non-chemokine agents identified by the above methods.

This invention provides a non-chemokine agent capable of binding to the chemokine receptor and inhibiting fusion of HIV-1 to CD4⁺ cells with the proviso that the agent is not a known bicyclam or its known derivatives. In an embodiment, the non-chemokine is a polypeptide. In a further embodiment, this polypeptide is a fragment of the chemokine RANTES (Gong et al., 1996). In a still further embodiment, the polypeptide may also comprise the RANTES sequence with deletion of the N-terminal amino acids of said sequence. The deletion may be the first eight N-terminal amino acids of the RANTES sequence (SEQ ID NO:5).

In a separate embodiment, the polypeptide may comprise the MIP-1β sequence with deletion of the N-terminal amino acids of said sequence. The deletion may be the first seven, eight, nine or ten N-terminal amino acids of the MIP-1β sequence.

In another embodiment of non-chemokine agent, the polypeptide comprises the MIP-1β sequence with the N-terminal sequence modified by addition of an amino acid or oligopeptide. In a separate embodiment, the polypeptide comprises the MIP-1β sequence with the N-terminal sequence modified by removing the N-terminal alanine and replaced it by serine or threonine and additional amino acid or oligopeptide or nonpeptidyl moiety. In a further embodiment, the additional amino acid is methionine.

As described infra in the section of Experimental Details, a cofactor for HIV-1 fusion and entry was identified and designated "fusin" (Feng et al., 1996). This invention provides an agent which is capable of binding to fusin and inhibiting infection. In an embodiment, the agent is an oligopeptide. In another embodiment, the agent is an polypeptide.

In a further embodiment, the polypeptide comprises SDF-1 with deletion of the N-terminal amino acids of said sequence. The deletion may be the first six, seven, eight, or nine N-terminal amino acids of the SDF-1 sequence.

This invention also provides the above non-chemokine agent, wherein the polypeptide comprises SDF-1 sequence with the N-terminal sequence modified to produce antagonistic effect to SDF-1. One modification is to replace the N-terminal glycine of SDF-1 by serine and derivatized with biotin. Another modification is to replace the N-terminal glycine of SDF-1 by serine and derivatized with methionine. A further modification is to add the N-terminus of SDF-1 with a methionine before the terminal glycine.

In still another embodiment, the agent is an antibody or a portion of an antibody. In a separate embodiment, the agent is a nonpeptidyl agent.

The agents capable of binding to fusin may be identified by screening different compounds for their capability to bind to fusin in vitro.

A suitable method has been described by Fowlkes, et al. (1994), international application number: PCT/US94/03143, international publication number: WO 94/23025, the content of which is incorporated by reference into this application. Briefly, yeast cells having a pheromone system are engineered to express a heterologous surrogate of a yeast pheromone system protein. The surrogate incorporates fusin and under some conditions performs in the pheromone system of the yeast cell a function naturally performed by the corresponding yeast pheromone system protein. Such yeast cells are also engineered to express a library of peptides whereby a yeast cell containing a peptide which binds fusin exhibits modulation of the interaction of surrogate yeast pheromone system protein with the yeast pheromone system and this modulation is a selectable or screenable event. Similar approaches may be used to identify agents capable of binding to both fusin and the chemokine receptor C—C CKR-5.

This invention also provides pharmaceutical compositions comprising an amount of such non-chemokine agents or agents capable of binding to fusin effective to inhibit fusion of HIV-1 to $CD4^+$ cells and a pharmaceutically acceptable carrier.

Pharmaceutically acceptable carriers are well known to those skilled in the art. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a composition of matter capable of binding to the chemokine receptor and inhibiting fusion of HIV-1 to $CD4^+$ cells comprising a non-chemokine agent linked to a ligand capable of binding to a cell surface receptor of the $CD4^+$ cells other than the chemokine receptor such that the binding of the non-chemokine agent to the chemokine receptor does not prevent the binding of the ligand to the other receptor. In an embodiment, the cell surface receptor is CD4. In another embodiment, the ligand is an antibody or a portion of an antibody.

This invention also provides a pharmaceutical composition comprising an amount of an above-described composition of matter effective to inhibit fusion of HIV-1 to $CD4^+$ cells and a pharmaceutically acceptable carrier.

This invention provides a composition of matter capable of binding to the chemokine receptor and inhibiting fusion of HIV-1 to CD4+cells comprising a non-chemokine agent linked to a compound capable of increasing the in vivo half-life of the non-chemokine agent. In an embodiment, the compound is polyethylene glycol.

This invention also provides a pharmaceutical composition comprising an amount of a composition of matter comprising a non-chemokine agent linked to a compound capable of increasing the in vivo half-life of the non-chemokine agent effective to inhibit fusion of HIV-1 to $CD4^+$ cells and a pharmaceutically acceptable carrier.

This invention provide methods for reducing likelihood of HIV-1 infection in a subject comprising administering the above-described pharmaceutical compositions to the subject. This invention also provides methods for treating HIV-1 infection in a subject comprising administering the above-described pharmaceutical compositions to the subject.

This invention also provides methods for determining whether a non-chemokine agent is capable of inhibiting the fusion of HIV-1 to a $CD4^+$ cell which comprise: (a) contacting (i) a $CD4^+$ cell which is labeled with a first dye and (ii) a cell expressing the HIV-1 envelope glycoprotein on its surface which is labeled with a second dye, in the presence of an excess of the agent under conditions permitting the fusion of the $CD4^+$ cell to the cell expressing the HIV-1 envelope glycoprotein on its surface in the absence of the agent, the first and second dyes being selected so as to allow resonance energy transfer between the dyes; (b) exposing the product of step (a) to conditions which would result in resonance energy transfer if fusion has occurred; and (c) determining whether there is a reduction of resonance energy transfer, when compared with the resonance energy transfer in the absence of the agent, a decrease in transfer indicating that the agent is capable of inhibiting fusion of HIV-1 to $CD4^+$ cells.

HIV-1 only fuses with appropriate $CD4^+$ cells. For example, laboratory-adapted T lymphotropic HIV-1 strains fuse with most $CD4^+$ human cells. Clinical HIV-1 isolates do not fuse with most transformed $CD4^+$ human cell lines but do fuse with human primary $CD4^+$ cells such as $CD4^+$ T lymphocytes and macrophages. Routine experiments may be easily performed to determine whether the CD4+cell is appropriate for the above fusion assay.

As described in this invention, HIV-1 membrane fusion is monitored by a resonance energy transfer assay. The assay was described in the International Application Number, PCT/US94/14561, filed Dec. 16, 1994 with International Publication Number WO 95/16789. This assay is further elaborated in a United States co-pending application no. 08/475,515, filed Jun. 7, 1995. The contents of these applications are hereby incorporated by reference into this application.

In an embodiment of the above method, the non-chemokine agent is an oligopeptide. In another embodiment, the non-chemokine agent is a polypeptide. In still another embodiment, the agent is an antibody or a portion thereof. In a further embodiment, the non-chemokine agent is a non-peptidyl agent.

In a separate embodiment, the CD4$^+$ cell is a PM1 cell. In another embodiment, the cell expressing the HIV-1 envelope glycoprotein is a HeLa cell expressing HIV-1$_{JR-FL}$ gp120/gp41.

This invention provides a method for determining whether an agent is capable of inhibiting HIV-1 infection comprising steps of: (a) fixing a chemokine receptor on a solid matrix; (b) contacting the agent with the fixed chemokine receptor under conditions permitting the binding of the agent to the chemokine receptor; (c) removing the unbound agent; (d) contacting the fixed chemokine receptor resulting in step (c) with a gp120 in the presence of CD4 under conditions permitting the binding of the gp120/CD4 complex and the chemokine receptor in the absence of the agent; (e) measuring the amount of bound gp120/CD4 complex; and (f) comparing the amount determined in step (d) with the amount determined in the absence of the agent, a decrease of the amount indicating that the agent is capable of inhibiting HIV-1 infection.

This invention also provides a method for determining whether an agent is capable of inhibiting HIV-1 infection comprising steps of: (a) fixing a chemokine receptor on a solid matrix; (b) contacting the agent with the fixed chemokine receptor; (c) contacting the mixture in step (b) with a gp120 in the presence of CD4 under conditions permitting the binding of the gp120/CD4 complex and the chemokine receptor in the absence of the agent; (d) measuring the amount of bound gp120/CD4 complex; and (e) comparing the amount determined in step (d) with the amount determined in the absence of the agent, a decrease of the amount indicating that the agent is capable of inhibiting HIV-1 infection.

This invention also provides a method for determining whether an agent is capable of inhibiting HIV-1 infection comprising steps of: (a) fixing a gp120/CD4 complex on a solid matrix; (b) contacting the agent with the fixed gp120/CD4 complex under conditions permitting the binding of the agent to the gp120/CD4 complex; (c) removing unbound agent; (d) contacting the fixed gp120/CD4 complex resulting from step (c) with a chemokine receptor under conditions permitting the binding of the gp120/CD4 complex and the chemokine receptor in the absence of the agent; (e) measuring the amount of bound chemokine receptor; and (f) comparing the amount determined in step (e) with the amount determined in the absence of the agent, a decrease of the amount indicating that the agent is capable of inhibiting HIV-1 infection.

This invention provides a method for determining whether an agent is capable of inhibiting HIV-1 infection comprising steps of: (a) fixing a gp120/CD4 on a solid matrix; (b) contacting the agent with the fixed gp120/CD4 complex; (c) contacting the mixture in step (b) with a chemokine receptor under conditions permitting the binding of the gp120/CD4 complex and the chemokine receptor in the absence of the agent; (d) measuring the amount of bound chemokine receptor; (e) comparing the amount determined in step (d) with the amount determined in the absence of the agent, a decrease of the amount indicating that the agent is capable of inhibiting HIV-1 infection.

As used in these assays, CD4 include soluble CD4, fragments of CD4 or polypeptides incorporating the gp120 binding site of CD4 capable of binding gp120 and enabling the binding of gp120 to the appropriate chemokine receptor.

As used in these assay gp120 is the gp120 from an appropriate strain of HIV-1. For example, gp120 from the macrophage tropic clinical isolate HIV-1$_{JR-FL}$ will bind to the chemokine receptor CCR5, whereas gp120 from the laboratory adapted T-tropic strain HIV-1$_{LAI}$ will bind to the chemokine receptor CXCR4.

In a preferred embodiment of the above methods, the CD4 is a soluble CD4. The chemokine receptor which may be used in the above assay includes CCR5, CXCR4, CCR3 and CCR-2b.

In an embodiment, the chemokine receptor is expressed on a cell. In a preferred embodiment, the cell is a L1.2 cell. In a separate embodiment, the chemokine receptor is purified and reconstituted in liposomes. Such chemokine receptor embedded in the lipid bilayer of liposomes retains the gp120 binding activity of the receptor.

The gp120, CD4 or both may be labelled with a detectable marker in the above assays. Markers including radioisotope or enzymes such as horse radish peroxidase may be used in this invention.

In an embodiment, the gp120 or CD4 or the chemokine receptor is labelled with biotin. In a further embodiment, the biotinylated gp120, or CD4 or the chemokine receptor is detected by: (i) incubating with streptavidin-phycoerythrin, (ii) washing the incubated mixture resulting from step (i), and (iii) measuring the amount of bound gp120 using a plate reader, exciting at 530 nm, reading emission at 590 nm.

This invention also provides an agent determined to be capable of inhibiting HIV-1 infection by the above methods, which is previously unknown.

This invention also provides a pharmaceutical composition comprising the agent determined to be capable of inhibiting HIV-1 infection by the above methods and a pharmaceutically acceptable carrier. In an embodiment, the agent is an oligopeptide. In another embodiment, the agent is a polypeptide. In a still another embodiment, the agent is a nonpeptidyl agent.

This invention also provides a molecule capable of binding to the chemokine receptor CCR5 and inhibiting fusion of HIV-1 to CD4$^+$ cells comprising the above determined agent linked to a compound capable of increasing the in vivo half-life of the non-chemokine agent. In an embodiment, the compound is polyethylene glycol. This invention also provides a pharmaceutical composition comprising an amount of the above molecule effective to inhibit HIV-1 infection and a pharmaceutically acceptable carrier.

This invention provides a method for reducing the likelihood of HIV-1 infection in a subject comprising administering the above pharmaceutical compositions to the subject.

This invention provides a method for treating HIV-1 infection in a subject comprising administering the above pharmaceutical composition to the subject.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

First Series of Experiments

1) Chemokines inhibit fusion mediated by the envelope glycoprotein from a macrophage-tropic primary isolate of HIV-1 but not from a laboratory-adapted T-lymphotrophic strain of the virus The chemokines RANTES, MIP-1α and MIP-1β were obtained from R & D systems (Minneapolis, Minn.). They were tested in the RET assay for ability to inhibit fusion between HeLa-env$_{JR-FL}$ cells (expressing gp120/gp41 from the macrophage tropic isolate HIV-1$_{JR-FL}$) and PM1 cells, or for inhibition of fusion between HeLa-env$_{LAI}$ cells (expressing gp120/gp41 from the laboratory-adapted strain HIV-1$_{LAI}$) and various CD4$^+$ T lymphocyte cell lines. As shown in FIG. 1, all three chemokines inhibited fusion mediated by the macrophage tropic virus envelope glycoprotein, but not that mediated by the laboratory-adapted strain envelope glycoprotein.

The ability of the chemokines to block the interaction between CD4 and HIV-1 gp120 which occurs at virus attachment was then tested. It was found that the chemokines did not inhibit this interaction (FIG. 2), demonstrating that their blockade of HIV-1 envelope glycoprotein-mediated membrane fusion occurs at the membrane fusion event itself, rather than the initial CD4-gp120 interaction which precedes fusion.

2) Non-chemokine peptides and derivatives that inhibit HIV-1 fusion

The non-chemokines include chemokine fragments and chemokine derivatives that are tested in the RET assay to determine which are active in inhibiting HIV-1 membrane fusion. Particular attention is focused on fragments or derivatives that inhibit HIV-1 fusion but do not activate leukocyte responses. These non-chemokines include:

a) N-terminal derivatives of the chemokines. Addition of residues to the N-terminus of chemokines inhibits the function of these proteins without significantly reducing their ability to bind chemokine receptors. For example, Met-RANTES (RANTES with an N-terminal methionine) has been shown to be a powerful antagonist of native RANTES and is unable to induce chemotaxis or calcium mobilization in certain systems. The mechanism of antagonism appears to be competition for receptor binding (9). Similar results were found using other derivatives of the N terminus of RANTES (9) and also by N-terminal modification of other chemokines, such as IL-8 (a member of the C-X-C chemokines) (10). The current invention includes Met-RANTES and other chemokines derivatised by the addition of methionine, or other residues, to the N-terminus so that they inhibit fusion mediated by the envelope glycoprotein of HIV-1$_{JR-FL}$, and inhibit infection by many isolates of HIV-1, yet do not activate the inflammatory response.

b) Chemokines with N-terminal amino acids deleted: Chemokine antagonists have been generated by deleting amino acids in the N-terminal region. For example, deletion of up to 8 amino acids at the N-terminus of the chemokine MCP-1 (a member of the C—C chemokine group), ablated the bioactivity of the protein while allowing it to retain chemokine receptor binding and the ability to inhibit activity of native MCP-1 (11,12).

The current invention includes N-terminal deletants of RANTES, MIP-1α and MIP-1β, lacking the biological activity of the native proteins, which inhibit HIV-1 fusion and HIV-1 infection.

c) Other peptides: A series of overlapping peptides (e.g. of 20–67 residues) from all regions of RANTES, MIP-1α and MIP-1β are screened by the same approaches to identify peptides which inhibit HIV-1 fusion most potently without activating leukocytes. Activation of leukocyte responses is measured following routine procedures (9, 10, 11, 12).

3) Cloning the chemokine receptors

Chemokine receptors required for HIV-1 fusion are cloned by the following strategy. First a cDNA library is made in a mammalian expression vector (e.g. pcDNA3.1 from Invitrogen Corp. San Diego, Calif.) using mRNA prepared from the PM1 cell line or CD4$^+$ T-lymphocytes or macrophages. Degenerate oligonucleotide probes are used to identify members of the cDNA library encoding members of the chemokine receptor family, for example following previously published methods (2). The vectors containing chemokine receptor cDNAs are then individually expressed in one of several mammalian cell lines which express human CD4 but do not fuse with HeLa-env$_{JR-FL}$ cells (e.g. HeLa-CD4, CHO-CD4 or COS-CD4) or HeLa-env$_{LAI}$ cells (e.g. CHO-CD4 or COS-CD4). Following analysis in the RET assay, clones which gain the ability to fuse with HeLa-env$_{JR-FL}$ or HeLa-env$_{LAI}$ are identified and the coding sequences recovered, for example by PCR amplification, following procedures well known to those skilled in the art. DNA sequencing is then performed to determine whether the cDNA recovered encodes a known chemokine receptor. Following expression of the receptor, monoclonal and polyclonal antibodies are prepared and tested for ability to inhibit infection by a panel of HIV-1 isolates.

References of the First Series of Experiments

1. Cocchi, F., DeVico, A. L., Garzino-Demo, A., Arya, S. K., Gallo, R. C., Lusso, P. 1995. *Science.* 270:1811–1815.

2. Raport, C. J., Schweickart, V. L., Chantry, D., Eddy Jr., R. L., Shows, T. B., Godiska, R., Gray, P. W. 1996. *Journal of Leukocyte Biology.* 59: 18–23.

3. Maddon P J., Dalgleish A G., McDougal J S., Clapham P R., Weiss R A., Axel R. 1986. *Cell.* 47:333–348.

4. Ashorn P A., Berger E A., Moss B. 1990. *J. Virol.* 64:2149–2156.

5. Clapham P R., Blanc D., Weiss R A. 1991. *Virology.* 181:703–715.

6. Harrington R D., Geballe A P. 1993. *J. Virol.* 67:5939–5947.

7. Broder C C., Dimitrov D S., Blumenthal R., Berger E A. 1993. *Virology.* 193:483–491.

8. Dragic T., Charneau P., Clavel F., Alizon M. 1992. *J. Virol.* 66:4794–4802.

9. Wells, T. N., Power, C. A., Lusti-Narasimhan, M., Hoogewerf, A. J., Cooke, R. M., Chung, C. W., Peitsch, M. C., Proudfoot, A. E. 1996. *Journal of Leukocyte Biology.* 59:53–60.

10. Moser, B., Dewald, B., Barella, L., Schumacher, C., Baggiolini, M., Clark-Lewis, I. 1993. *Journal of Biological Chemistry.* 268:7125–7128.

11. Gong, J. H., Clark-Lewis, I. 1995. *J. Exp. Med.* 181:631–640.

12. Zhang, Y. J., Rutledge, B. J., Rollins, B. J. 1994. *Journal of Biological Chemistry.* 269:15918–15924.

13. Merrifield, R. B. (1963) *J. Am. Chem. Soc.* 85: 2149–2154.

14. Goeghegan, K. F. Stroh, J. F. (1992) *Bioconjugate Chem.* 3: 138–146.

15. Clercq, E. D. et al. (1994) *Antimicrobial Agents and Chemotherapy* 38:668–674.

16. Clercq, E. D. et al (1992) *Proc. Natl. Acad. Sci. USA* 89: 5286–5290.

Second Series of Experiments

The replication of primary, non-syncytium-inducing (NSI) HIV-1 isolates in CD4+ T-cells is inhibited by the C—C β-chemokines MIP-1a, MIP-1β and RANTES (1,2), but T-cell line-adapted (TCLA) or syncytium-inducing (SI) primary strains are insensitive (2,3). The β-chemokines are small (8 kDa), related proteins active on cells of the lymphoid and monocyte lineage (4–8). Their receptors are members of the 7-membrane-spanning, G-protein-linked superfamily, one of which (the LESTR orphan receptor) has been identified as the second receptor for TCLA HIV-1 strains, and is now designated fusin (9). Fusin is not known to be a β-chemokine receptor (7–9).

To study how β-chemokines inhibit HIV-1 replication, a virus entry assay based on single-cycle infection by an env-deficient virus, NL4/3Δenv (which also carries the luciferase reporter gene), complemented by envelope glycoproteins expressed in trans was used (10,11). Various env-complemented viruses were tested in PM1 cells, a variant of HUT-78 that has the unique ability to support replication of primary and TCLA HIV-1 strains, allowing comparison of envelope glycoprotein functions against a common cellular background (2,12). MIP-1α, MIP-1β and RANTES are most active against HIV-1 in combination (2,3), and strongly inhibited infection of PM1 cells by complemented viruses whose envelopes are derived from the NSI primary strains ADA and BaL (Table 1a).

TABLE 1

Inhibition of HIV-1 entry in PM1 cells and CD4+ T-cells by β-chemokines

| | % luciferase activity | | | | |
|---|---|---|---|---|---|
| | BaL | ADA | NL4/3 | HxB2 | MuLV |
| a) PM1 cells | | | | | |
| control without virus | 2 | 2 | 2 | 5 | 3 |
| control with virus | 100 | 100 | 100 | 100 | 100 |
| +R/Mα/Mβ (50/50/50) | 2 | 3 | 92 | 117 | 100 |
| +RANTES (100) | 1 | 1 | nd | nd | nd |
| +MIP-1α (100) | 54 | 54 | nd | nd | nd |
| +MIP-1β (100) | 1 | 6 | nd | nd | nd |
| +MCP-1 (100) | 46 | 50 | nd | nd | nd |
| +MCP-2 (100) | 28 | 26 | nd | nd | nd |
| +MCP-3 (100) | 58 | 46 | nd | nd | nd |
| b) | JR-FL | HxB2 | MuLV | | |
| LW4 CD4+ T-cells | | | | | |
| control without virus | 1 | 1 | 1 | | |
| control with virus | 100 | 100 | 100 | | |
| +R/Mα/Mβ (200/200/200) | 14 | 68 | nd | | |
| LW5 CD4+ T-cells | | | | | |
| control without virus | 1 | 1 | 1 | | |
| control with virus | 100 | 100 | 100 | | |
| +R/Mα/Mβ (200/200/200) | 15 | 73 | nd | | |

Table 1 legend:

PM1 cells were cultured as described by Lusso et al (12). Ficoll/hypaque-isolated PBMC from laboratory workers (LW) stimulated with PHA for 72h before depletion of CD8+ Lymphocytes with anti-CD8 immunomagnetic beads (DYNAL, Great Neck, N.Y.). CD4+ Lymphocytes were maintained in culture medium containing interleukin-2 (100U/ml; Hofmann LaRoche, Nutley, N.J.), as described previously (3). Target cells ($1-2\times10^5$) were infected with supernatants (10–50 ng of HIV-1 p24) from 293-cells co-transfected with an NL4/3Δenv-luciferase vector and a HIV-1 env-expressing vector (10,11). β-Chemokines (R & D Systems, Minneapolis) were added to the target cells simultaneously with virus, at the final concentrations (ng/ml) indicated in parentheses in the first column. The β-chemokine concentration range was selected based on prior studies (2,3). After 2 h, the cells were washed twice with PBS, resuspended in β-chemokine-containing media and maintained for 48–96 h. Luciferase activity in cell lysates was measured as described previously (10, 11). The values indicated represent luciferase activity (cpm)/ng p24/mg protein, expressed relative to that in virus-control cultures lacking β-chemokines (100%), and are the means of duplicate or sextuplicate determinations. nd, not done. R/Mα/Mβ, RANTES+ MIP-1α+MIP-1β.

RANTES and MIP-1β were strongly active when added individually, while other β-chemokines—MIP-1α, MCP-1, MCP-2 and MCP-3 (refs. 13–15)—were weaker inhibitors (Table 1a). However, MIP-1α, MIP-1β and RANTES, in combination, did not inhibit infection of PM1 cells by the TCLA strains NL4/3 and HxB2, or by the amphotropic murine leukemia virus (MuLV-Ampho) pseudotype (Table 1a). Thus, phenotypic characteristics of the HIV-1 envelope glycoproteins influence their sensitivity to β-chemokines in a virus entry assay.

The env-complementation assay was used to assess HIV-1 entry into CD4+ T-cells from two control individuals (LW4 and LW5). MIP-1a, MIP-1β and RANTES strongly inhibited infection by the NSI primary strain JR-FL infection of LW4's and LW5's CD4+ T-cells, and weakly reduced HxB2 infection of LW cells (Table 1b), suggesting that there may be some overlap in receptor usage on activated CD4+ T-cells by different virus strains. BaL env-mediated replication in normal PBL was also inhibited by MIP-$_1$α, MIP-1β and RANTES, albeit with significant inter-donor variation in sensitivity (data not shown).

It was determined when β-chemokines inhibited HIV-1 replication by showing that complete inhibition of infection of PM1 cells required the continuous presence of β-chemokines for up to 5 h after addition of ADA or BaL env-complemented virus (FIG. 3a). Pre-treatment of the cells with β-chemokines for 2 h or 24 h prior to infection had no inhibitory effect if the cells were subsequently washed before virus addition. Furthermore, adding β-chemokines 2 h after virus only minimally affected virus entry (FIG. 3a). A PCR-based assay was next used to detect HIV-1 early DNA reverse transcripts in PM1 cells after 10 h of infection; reverse transcription of ADA, but not of NL4/3, could not be detected in the presence of MIP-1β and RANTES (FIG. 3b). Thus, inhibition by β-chemokines requires their presence during at least one of the early stages of HIV-1 replication: virus attachment, fusion and early reverse transcription.

As described in part in the First Series of Experiments, these sites of action were discriminated, first by testing whether β-chemokines inhibited binding of JR-FL or BRU (LAI) gp120 to soluble CD4, or of tetrameric CD4-IgG2 binding to HeLa-JR-FL cells expressing oligomeric envelope glycoproteins (17). No inhibition by any of the β-chemokines was found in either assay, whereas the OKT4a CD4-MAb was strongly inhibitory in both (FIG. 2 and data not shown). Thus, β-chemokines inhibit a step after CD4 binding, when conformational changes in the envelope glycoproteins lead to fusion of the viral and cellular membranes (18). Cell-cell membrane fusion is also induced by the gp120-CD4 interaction, and can be monitored directly by resonance energy transfer (RET) between fluorescent dyes incorporated into cell membranes (17). In the RET assay, OKT4a completely inhibits membrane fusion of PM1 cells with HeLa cells expressing the envelope glycoproteins of either JR-FL (HeLa-JR-FL, the same cell line referred to above as HeLa-env$_{JR-FL}$) or BRU (HeLa-BRU, the same cell line referred to above as HeLa-env$_{LAI}$), confirming the specificity of the process (17). RANTES, MIP-1β (and to a lesser extent, MIP-1β) strongly inhibited membrane fusion of HeLa-JR-FL cells with PM1 cells, whereas fusion between PM1 cells and HeLa-BRU cells was insensitive to these β-chemokines (FIG. 1 and Table 2a).

TABLE 2

Effect of β-chemokines on HIV-1 envelope glycoprotein-mediated membrane fusion measured using the RET assay

| | % Fusion | |
|---|---|---|
| | HeLa-JR-FL | HeLa-BRU |
| a) PM1 cells | | |
| no chemokines | 100 | 100 |
| +R/Mα/Mβ (80/400/100) | 1 | 95 |
| +RANTES (80) | 8 | 100 |
| +MIP-1α (400) | 39 | 100 |
| +MIP-1β (100) | 13 | 93 |
| +MCP-1 (100) | 99 | 98 |
| +MCP-2 (100) | 72 | 93 |
| +MCP-3 (100) | 98 | 99 |
| b) LW5 CD4$^+$ cells | | |
| no chemokines | 100 | 100 |
| +R/Mα/Mβ (106/533/133) | 39 | 100 |
| +RANTES (106) | 65 | 95 |
| +MIP-1α (533) | 72 | 100 |
| +MIP-1β (133) | 44 | 92 |
| +OKT4A (3ug/ml) | 0 | 0 |

Table 2 legend:
CD4$^+$ target cells (mitogen-activated CD4$^+$ lymphocytes or PM1 cells) were labeled with octadecyl rhodamine (Molecular Probes, Eugene, Oreg.), and HeLa-JR-FL cells, HeLa-BRU cells (or control HeLa cells, not shown) were labeled with octadecyl fluorescein (Molecular Probes), overnight at 37° C. Equal numbers of labeled target cells and env-expressing cells were mixed in 96-well plates and B-chemokines (or CD4 MAb OKT4a) were added at the final concentrations (ng/ml) indicated in parentheses in the first column. Fluorescence emission values were determined 4 h after cell mixing (17). If cell fusion occurs, the dyes are closely associated in the conjoined membrane such that excitation of fluorescein at 450 nm results in resonance energy transfer (RET) and emission by rhodamine at 590nm. Percentage fusion is defined as equal to 100×[(Exp RET−Min RET)/(Max RET−Min RET)], where Max RET=% RET obtained when HeLa-Env and CD4$^+$ cells are mixed, Exp RET=% RET obtained when HeLa-Env and CD4$^+$ cells are mixed in the presence of fusion-inhibitory compounds, and Min RET=% RET obtained when HeLa cells (lacking HIV-1 envelope glycoproteins) and CD4$^+$ cells are mixed. The % RET value is defined by a calculation described elsewhere (17), and each is the mean of triplicate determinations. These values were, for HeLa-JR-FL and HeLa-BRU cells respectively: PM1 cells 11.5%, 10.5%; LW5 CD4$^+$ cells, 6.0%, 10.5%; R/Mα/Mβ, RANTES+MIP-1α+MIP-1β.

Similar results were obtained with primary CD4$^+$ T-cells from LW5 (Table 2b), although higher concentrations of β-chemokines were required to inhibit membrane fusion in the primary cells than in PM1 cells. Thus, the actions of the β-chemokines are not restricted to the PM1 cell line. The RET assay demonstrates that β-chemokines interfere with env-mediated membrane fusion.

The simplest explanation of these results is that the binding of certain β-chemokines to their receptor(s) prevents, directly or otherwise, the fusion of HIV-1 with CD4$^+$ T-cells. It has been known for a decade that HIV-1 requires a second receptor for entry into CD4+cells (19–21). This function is supplied, for TCLA strains, by fusin (9). Several receptors for MIP-1α, MIP-1β and RANTES have been identified (6,7), and β-chemokines exhibit considerable cross-reactivity in receptor usage (4–8). However, C—C CKR-1 and, especially, C—C CKR-5 were identified as the most likely candidates, based on tissue expression patterns and their abilities to bind MIP-1α, MIP-1β and RANTES (4,7,8,15,22). C—C CKR-1, C—C CKR-5 and LESTR are each expressed at the MRNA level in PM1 cells and primary macrophages (data not shown). These and other β-chemokine receptors were therefore PCR-amplified, cloned and expressed.

The expression of C—C CKR-5 in HeLa-CD4 (human), COS-CD4 (simian) and 3T3-CD4 (murine) cells rendered each of them readily infectible by the primary, NSI strains ADA and BaL in the env-complementation assay of HIV-1 entry (Table 3).

TABLE 3

C-C CKR-5 expression permits infection of CD4-expressing cells by primary, NSI HIV-1 strains

| | | pcDNA3.1 | LESTR | CKR-1 | CKR-2a | CKR-3 | CKR-4 | CKR-5 | R/Mα/Mβ CKR-5 |
|---|---|---|---|---|---|---|---|---|---|
| COS-CD4 | ADA | 798 | 456 | 600 | 816 | 516 | 534 | 153000 | 3210 |
| | BaL | 660 | 378 | 600 | 636 | 516 | 618 | 58800 | 756 |
| | HxB2 | 5800 | 96700 | 5240 | 5070 | 5470 | 5620 | 4850 | 5000 |
| HeLa-CD4 | ADA | 678 | 558 | 4500 | 912 | 558 | 600 | 310000 | 6336 |
| | BaL | 630 | 738 | 1800 | 654 | 516 | 636 | 104000 | 750 |
| | HxB2 | 337000 | nd | nd | nd | nd | nd | nd | 356000 |
| 3T3-CD4 | ADA | 468 | 558 | 450 | 618 | 534 | 606 | 28400 | 1220 |
| | BaL | 606 | 738 | 660 | 738 | 534 | 558 | 11700 | 756 |
| | HxB2 | 456 | 24800 | 618 | 672 | 732 | 606 | 618 | 606 |

Table 3 legend:

Chemokine receptor genes C—C CKR-1, C-C CKR-2a, C—C CKR-3, C—C CKR-4 and C—C CKR-5 have no introns (4–8,15,22) and were isolated by PCR performed directly on a human genomic DNA pool derived from the PBMC of seven healthy donors. Oligonucleotides overlapping the ATG and the stop codons and containing BamHI and XhoI restriction sites for directional cloning into the pcDNA3.1 expression vector (Invitrogen Inc.) were used. LESTR (also known as fusin or HUMSTR) (4,9,24) was cloned by PCR performed directly on cDNA derived from PM1 cells, using sequences derived from the NIH database. Listed below are the 5' and 3' primer pairs used in first (5-1 and 3-1) and second (5-2 and 3-2) round PCR amplification of the CKR genes directly from human genomic DNA, and of LESTR from PM1 cDNA. Only a single set of primers was used to amplify CKR-5.

LESTR: L/5-1=AAG CTT GGA GAA CCA GCG GTT ACC ATG GAG GGG ATC (SEQ ID NO: 6);
L/5-2 =GTC TGA GTC TGA GTC AAG CTT GGA GAA CCA (SEQ ID NO: 7);
L/3-1 =CTC GAG CAT CTG TGT TAG CTG GAG TGA AAA CTT GAA GAC TC (SEQ ID NO: 8);
L/3-2 =GTC TGA GTC TGA GTC CTC GAG CAT CTG TGT (SEQ ID NO: 9);
CKR-1:C1/5-1=AAG CTT CAG AGA GAA GCC GGG ATG GAA ACT CC (SEQ ID NO: 10);
C1/5-2 =GTC TGA GTC TGA GTC AAG CTT CAG AGA GAA (SEQ ID NO: 11);
C1/3-1=CTC GAG CTG AGT CAG AAC CCA GCA GAG AGT TC (SEQ ID NO: 12);
C1/3-2=GTC TGA GTC TGA GTC CTC GAG CTG AGT CAG (SEQ ID NO: 13);
CKR-2a:C2/5-1=AAG CTT CAG TAC ATC CAC AAC ATG CTG TCC AC (SEQ ID NO: 14);
C2/5-2=GTC TGA GTC TGA GTC AAG CTT CAG TAC ATC (SEQ ID NO: 15);
C2/3-1 =CTC GAG CCT CGT TTT ATA AAC CAG CCG AGA C (SEQ ID NO: 16);
C2/3-2=GTC TGA GTC TGA GTC CTC GAG CCT CGT TTT (SEQ ID NO: 17);
CKR-3: C3/5-1=AAG CTT CAG GGA GAA GTG AAA TGA CAA CC (SEQ ID NO: 18);
C3/5-2=GTC TGA GTC TGA GTC AAG CTT CAG GGA GAA (SEQ ID NO: 19);
C3/3-1=CTC GAG CAG ACC TAA AAC ACA ATA GAG AGT TCC (SEQ ID NO: 20);
C3/3-2=GTC TGA GTC TGA GTC CTC GAG CAG ACC TAA (SEQ ID NO: 21);
CKR-4: C4/5-1=AAG CTT CTG TAG AGT TAA AAA ATG AAC CCC ACG G (SEQ ID NO: 22);
C4/5-2 =GTC TGA GTC TGA GTC AAG CTT CTG TAG AGT (SEQ ID NO: 23);
C4/3-1 =CTC GAG CCA TTT CAT TTT TCT ACA GGA CAG CAT C (SEQ ID NO: 24);
C4/3-2=GTC TGA GTC TGA GTC CTC GAG CCA TTT CAT (SEQ ID NO: 25);
CKR-5: C5/5-12=GTC TGA GTC TGA GTC AAG CTT AAC AAG ATG GAT TAT CAA (SEQ ID NO: 26);
C5/3-12=GTC TGA GTC TGA GTC CTC GAG TCC GTG TCA CAA GCC CAC (SEQ ID NO: 37).

The human CD4-expressing cell lines HeLa-CD4 (P42), 3T3-CD4 (sc6) and COS-CD4 (Z28T1) (23) were transfected with the different pcDNA3.1-CKR constructs by the calcium phosphate method, then infected 48h later with different reporter viruses (200 ng of HIV-1 p24/$10^6$ cells) in the presence or absence of β-chemokines (400 ng/ml each of RANTES, MIP-1α and MIP-1β). Luciferase activity in cell lysates was measured 48 h later (10,11). β-Chemokine blocking data is only shown for C—C CKR-5, as infection mediated by the other C—C CKR genes was too weak for inhibition to be quantifiable. In PCR-based assays of HIV-1 entry, a low level of entry of NL4/3 and ADA into C—C CKR-1 expressing cells (data not shown) was consistently observed.

Neither LESTR nor C—C CKR-1, -2a, -3 or -4 could substitute for C—C CKR-5 in this assay. The expression of LESTR in COS-CD4 and 3T3-CD4 cells permitted HxB2 entry, and HxB2 readily entered untransfected (or control plasmid-transfected) HeLa-CD4 cells (Table 3). Entry of BAL and ADA into all three C-C CKR-5-expressing cell lines was almost completely inhibited by the combination of MIP-1α, MIP-1β and RANTES, whereas HxB2 entry into LESTR-expressing cells was insensitive to β chemokines (Table 3). These results suggest that C—C CKR-5 functions as a β-chemokine-sensitive second receptor for primary, NSI HIV-1 strains.

The second receptor function of C—C CKR-5 was confirmed in assays of env-mediated membrane fusion. When C—C CKR-5 was transiently expressed in COS and HeLa cell lines that permanently expressed human CD4, both cell lines fused strongly with HeLa cells expressing the JR-FL envelope glycoproteins, whereas no fusion occurred when control plasmids were used (data not shown). Expression of LESTR instead of C-C CKR-5 did not permit either COS-CD4 or HeLa-CD4 cells to fuse with HeLa-JR-FL cells, but did allow fusion between COS-CD4 cells and HeLa-BRU cells (data not shown).

The fusion capacity of S-chemokine receptors was also tested in the RET assay. The expression of C—C CKR-5, but not of C—C CKR-1, -2a, -3 or -4, permitted strong fusion between HeLa-CD4 cells and HeLa-JR-FL cells. The extent of fusion between HeLa-JR-FL cells and C—C CKR-5-expressing HeLa-CD4 cells was greater than the constitutive level of fusion between HeLa-BRU cells and HeLa-CD4 cells (FIG. 4). The fusion-conferring function of C—C CKR-5 for primary, NSI HIV-1 strains has therefore been confirmed in two independent fusion assays.

Experimental Discussion

Together, the above results establish that MIP-1α, MIP-1β and RANTES inhibit HIV-1 infection at the entry stage, by interfering with the virus-cell fusion reaction subsequent to CD4 binding. It was also shown that C—C CKR-5 can serve as a second receptor for entry of primary NSI strains of HIV-1 into CD4+ T-cells, and that the interaction of β-chemokines with C—C CKR-5 inhibits the HIV-1 fusion reaction.

References of the Second Series of Experiments

1. Levy, J. A., Mackewicz, C. E. & Barker, E. Immunol. Today 17, 217–224 (1996).
2. Cocchi, F. et al. Science 270, 1811–1815 (1995).
3. Paxton, W. A. et al. Nat. Med. 2, 412–417 (1996).
4. Neote, K., DiGregorio, D., Mak, J. Y., Horuk, R., & Schall, T. J. Cell 72, 415–425 (1993).
5. Gao, J. -L. et al. J . Exp. Med. 177, 1421–1427 (1993).
6. Bacon, K. B., Premack, B. A., Gardner, P. & Schall, T. J. Science 269, 1727–1729 (1995).
7. Raport, C. J. etal. J. Leukoc. Biol. 59,18–23 (1996).
8. Wells, T. N. C. et al. J. Leukoc. Biol. 59, 53–60 (1996).
9. Feng, Y., Broder, C. C., Kennedy, P. E. & Berger, E. A. Science 272, 872–877 (1996).
10. Chen, B. K., Saksela, K., Andino, R. & Baltimore, D. J. Virol. 68, 654–660 (1994).

11. Connor, R. I., Chen, B. K., Choe, S., & Landau, N. R. Virology 206, 935–944 (1995).
12. Lusso,P. etal. J. Virol. 69, 3712–3720 (1995).
13. Charo, 1. F. et al. Proc. Natl. Acad. Sci. USA 91, 2752–2756 (1994).
14. Ben-Baruch, A. et al. J. Biol. Chem. 270, 22123–22128 (1995).
15. Combadiere, C etal. J. Biol. Chem. 270, 29671–29675 (1995).
16. Lip, J. P., D'Andrea, A. D., Lodish, H. F. & Baltimore, D. Nature 343, 762–764 (1990).
17. Litwin, V. et al. J. Virol. (submitted for publication).
18. Moore, J. P., Jameson, B. A., Weiss, R. A. & Sattentau, Q. J. in Viral Fusion Mechanisms (ed Bentz, J.) 233–289 (CRC Press Inc, Boca Raton, USA,1993).
19. Maddon, P. J. et al. Cell 47, 333–348 (1986).
20. Ashorn, P. A., Berger, E. A. & Moss, B. J. Virol. 64, 2149–2156 (1990).
21. Clapham, P. R., Blanc, D. & Weiss, R. A. Virology 181, 703–715 (1991).
22. Samson, M., Labbe, O., Mollereau, C., Vassart, G. & Parmentier, M. Biochemistry 11, 3362–3367 (1996).
23. Dragic, T., Charneau, P., Clavel, F. & Alizon, M. J. Virol. 66, 4794–4802 (1992)
24. Loetscher, M. et al. J. Biol. Chem. 269, 232–237 (1994).
25. Moore, J. P. & Ho, D. D. AIDS 9 (suppl A), S117–S136 (1995).
26. Trkola, A. & Moore, J. P. (unpublished data).
27. Chaudhuri, A., et al. 1994. J. Biol. Chem. 269, 7835–7838 (1994).
28. Neote, K., Mak, J. Y., Kolakowski Jr., L. F. & Schall, T. J. Blood 84, 44–52 (1994).
29. Dragic, T., Picard, L. & Alizon, M. J. Virol. 69, 1013–1018 (1995).
30. Puri, A., Morris, S. J., Jones, P., Ryan, M. & Blumenthal, R. Virology 219, 262–267 (1996).31

Third Series of Experiments

The chemokine SDF-1 (stromal cell-derived factor 1) is the natural ligand for Fusin/CXCR4 and blocks infection by laboratory-adapted strains of HIV-1 (Ref. 1 and 2). SDF-1 exists as at least two forms, SDF-1α and SDF-1β based on variable splicing of the SDF-1 gene (Ref. 1 and 3) In the RET assay, this chemokine specifically inhibits membrane fusion mediated by gp120/gp41 form the laboratory-adapted strain HIV$_{LAI}$ but not by gp120/gp41 from the macrophage-tropic isolate HIV-1$_{JR-FL}$ as shown in FIG. 5.

References of the Third Series of Experiments

1. Bleul, C. C., et al. (1996) *Nature* 382:829–833
2. Oberlin, E., et al. (1996) *Nature* 382:833–835
3. Shirozu, M., et al. (1995) *Genomics* 28:495–500

Fourth Series of Experiments

Direct Binding of HIV-1$_{JR-FL}$ gp120 to CCR5$^+$ CD4$^-$ Cells

The direct binding of HIV-1$_{JR-FL}$ gp120 to CCR5$^+$ CD4$^-$ cells has been demonstrated. In this case, preincubation of the gp120 with sCD4 or another CD4-based molecule is required, presumably because this results in a conformational change in gp120 that exposes a chemokine receptor binding site. FIG. 6 illustrates the use of flow cytometry to measure the direct binding of sCD4/gp120 complexes to human CCR5-bearing murine L1.2 cells. Background levels of binding were observed with either biotinylated protein alone, or if gp120 from the laboratory-adapted strain HIV-1$_{LAI}$ is used in place of the HIV-1$_{JR-FL}$ gp120 (data not shown).

This assay has been adapted for drug screening purposes to a 96-well microplate format where binding of the sCD4/gp120 complexes to CCR5$^+$/CD4$^-$ cells is measured using a fluorometric plate reader. One method is as follows:

1) Plate out L1.2-CCR5+cells (approx. 500,000/well).
2) Add inhibitor for 1 hour at room temperature.
3) Wash and add biotinylated sCD4(2.5 μg/ml) and biotinylated HIV-1$_{JR-FL}$ gp120 (5 μg/ml), then incubate for 2 hours at room temperature.
4) Wash and incubate with streptavidin-phycoerythrin (100 ng/nl).
5) Wash and measure the amount of bound gp120/sCD4 using a fluorometric plate reader exciting at 530 nm and reading emission at 590 nm.

Using this method, inhibition of binding of gp120/sCD4 to CCR5 by CC-chemokines (FIG. 7) and antibodies to CCR5 that block HIV-1 infection (not shown) have been demonstrated.

Inhibition of HIV-1 envelope-mediated membrane fusion by the bicyclam, JM3100.

The bicyclam JM3100, obtained from Dr. J. Moore (Aaron Diamond AIDS Research Center, NY) was tested for ability to inhibit membrane fusion mediated by the envelope glycoproteins of the LAI or JR-FL strains of HIV-1 using the resonance energy transfer (RET) assay described above. As illustrated in FIG. 7, this molecule specifically and potently inhibits fusion mediated by gp120/gp41 from the HIV-1$_{LAI}$ strain, and not from the HIV-1$_{JR-FL}$ strain. These data suggest that this molecule specifically inhibits HIV fusion by blocking the interaction between HIV-1$_{LAI}$ gp120 and CXCR4.

---

What is claimed is:

1. An in vitro method for determining whether an agent is capable of inhibiting HIV-1 infection of a $CD4^+$ cell susceptible to HIV-1 infection comprising the steps of:
   (a) fixing a chemokine receptor on a solid matrix wherein the chemokine receptor is a co-receptor for HIV-1 infection;
   (b) contacting the fixed chemokine receptor with the agent under conditions permitting binding of the agent to the chemokine receptor;
   (c) removing any unbound agent;
   (d) contacting the resulting fixed chemokine receptor to which the agent is bound with a predetermined amount of $gp120/CD4^+$ complex under conditions permitting binding of $gp120/CD4^+$ complex to the fixed chemokine receptor in the absence of the agent;
   (e) removing any unbound $gp120/CD4^+$ complex;
   (f) measuring the amount of $gp120/CD4^+$ complex bound to the fixed chemokine receptor; and
   (g) comparing the amount measured in step (f) with the amount measured in the absence of the agent, a decrease in the amount bound in the presence of the agent indicating that the agent is capable of inhibiting HIV-1 infection.

2. An in vitro method for determining whether an agent is capable of inhibuting HIV-1 infection of a $CD4^+$ cell susceptible to HIV-1 infection comprising the steps:
   (a) fixing a chernokine receptor on a solid matrix wherein the chemokine receptor is a co-receptor for HIV-1 infection;
   (b) contacting the fixed chemokine receptor with the agent and a predetermined amount of $gp120/CD4^+$ complex under conditions permitting binding of the $gp120/CD4^+$ complex to the fixed chemokine receptor in the absence of the agent;
   (c) removing any unbound agent or unbound $gp120/CD4^+$ complex or both;
   (d) measuring the amount of $gp120/CD4^+$ complex bound to the fixed chemokine receptor; and
   (e) comparing the amount measured in step (d) with the amount measured in the absence of the agent, a decrease in the amount bound in the presence of the agent indicating that the agent is capable of inhibiting HIV-1 infection.

3. An in vitro method for determining whether an agent is capable of inhibiting HIV-1 infection of a $CD4^+$ cell susceptible to HIV-1 infection comprising steps of:
   (a) fixing a $gp120/CD4^+$ complex on a solid matrix;
   (b) contacting the fixed $gp120/CD4^+$ complex with the agent under conditions permitting the binding of the agent to the $gp120/CD4^+$ complex;
   (c) removing any unbound agent;
   (d) contacting the resulting fixed $gp120/CD4^+$ complex to which the agent is bcund with a predetermined amount of chemokine receptor, wherein the chemokine receptor is a co-receptor for HIV-1 infection, under conditions permitting binding of the chemokine receptor to the fixed the $gp120/CD4^+$ complex in the absence of the agent;
   (e) removing any unbound chemokine receptor;
   (f) measuring the amount of chemokine receptor bound to the fixed $gp120/CD4^+$; and
   (g) comparing the amount measured in step (f) with the amount measured in the absence of the agent, a decrease in the amount bound in the presence of the agent indicating that the agent is capable of inhibiting HIV-1 infection.

4. An in vitro method for determining whether an agent is capable of inhibiting HIV-l infection of a $CD4^+$ cell susceptible to HIV-1 infection comprising steps of:
   (a) fixing a $gp120/CD4^+$ complex on a solid matrix:
   (b) contacting the fixed $gp120/CD4^+$ complex with the agent and a predetermined amount of chemokine receptor, wherein the chemokine receptor is a co-receptor for HIV-1 infection, under co)nditions permitting binding of the chemokine receptor to the fixed $gp120/CD4^+$ complex in the absence of the agent;
   (c) removing any unbound agent or any unbound chemokine receptor or both:
   (d) measuring the amount of chemorkine receptor bound to the fixed $gp120/CD4^+$; and
   (e) comparing the amount measured in step (d) with the amount measured in the absence of the agent, a decrease in the amount bound in the presence of the agent indicating that the agent is capable of inhibiting HIV-1 infection.

5. The method of claim 1, 2, 3, or 4 wherein the $CD4^+$ is a soluble $CD4^+$.

6. The method of claim 1, 2, 3, or 4 wherein the chemokine receptor is expressed on a cell.

7. The method of claim 6 wherein the cell is a L1.2 cell.

8. The method of claim 1 or 2, wherein the gp120, $CD4^+$ or both are labeled with a detectable marker.

9. The method of claim 3 or 4 wherein the chemokine receptor is labeled with a detectable marker.

10. The method of claim 1 or 2, wherein the gp120, $CD4^+$ or both are labeled with biotin.

11. The method of claim 2 or 4 wherein the chemokine receptor is labeled with biotin.

12. The method of any one of claims 1, 2, 3, or 4, wherein the chemockine receptor is CCR5.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 38 nucleotides
      (B) TYPE: nucleic acid

```
        (C) STRANDEDNESS: single
        (D) TOPOLOGY: linear (ii) MOLECULE TYPE: oligonucleotide (xi) SEQUENCE DESCRIPTION: SEQ ID NO:1:

CAAGGCTACT TCCCTGATTG GCAGAACTAC ACACCAGG                              38

(2) INFORMATION FOR SEQ ID NO:2:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:2:

AGCAAGCCGA GTCCTGCGTC GAGAG                                           25

(2) INFORMATION FOR SEQ ID NO:3:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:3:

GGGACTTTCC GCTGGGGACT TTC                                             23

(2) INFORMATION FOR SEQ ID NO:4:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

CCTGTTCGGG CGCCACTGCT AGAGATTTTC CAC                                  33

(2) INFORMATION FOR SEQ ID NO:5:

(i) SEQUENCE CHARACTERISTICS:
        (A) LENGTH: 60 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

Pro Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe Val
            20                  25                  30

Thr Arg Lys Asn Arg Gln Val Cys Ala Asn Pro Glu Lys Lys Trp Val Arg
35                  40                  45                  50

Glu Tyr Ile Asn Ser Leu Glu Met Ser
                55                  60
```

(2) INFORMATION FOR SEQ ID NO:6:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

AAGCTTGGAG AACCAGCGGT TACCATGGAG GGGATC                          36

(2) INFORMATION FOR SEQ ID NO:7:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

GTCTGAGTCT GAGTCAAGCT TGGAGAACCA                                   30

(2) INFORMATION FOR SEQ ID NO:8:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

CTCGAGCATC TGTGTTAGCT GGAGTGAAAA CTTGAAGACT C                   41

(2) INFORMATION FOR SEQ ID NO:9:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

GTCTGAGTCT GAGTCCTCGA GCATCTGTGT                                   30

(2) INFORMATION FOR SEQ ID NO:10:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

AAGCTTCAGA GAGAAGCCGG GATGGAAACT CC                               32

(2) INFORMATION FOR SEQ ID NO:11:

(i) SEQUENCE CHARACTERISTICS:

(A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

GTCTGAGTCT GAGTCAAGCT TCAGAGAGAA                     30

(2) INFORMATION FOR SEQ ID NO:12:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CTCGAGCTGA GTCAGAACCC AGCAGAGAGT TC                  32

(2) INFORMATION FOR SEQ ID NO:13:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

GTCTGAGTCT GAGTCCTCGA GCTGAGTCAG                     30

(2) INFORMATION FOR SEQ ID NO:14:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

AAGCTTCAGT ACATCCACAA CATGCTGTCC AC                  32

(2) INFORMATION FOR SEQ ID NO:15:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:15:

GTCTGAGTCT GAGTCAAGCT TCAGTACATC                     30

(2) INFORMATION FOR SEQ ID NO:16:

(i) SEQUENCE CHARACTERISTICS:
        (A) LENGTH: 31 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:16:

CTCGAGCCTC GTTTTATAAA CCAGCCGAGA C                                              31

(2) INFORMATION FOR SEQ ID NO:17:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:17:

GTCTGAGTCT GAGTCCTCGA GCCTCGTTTT                                                30

(2) INFORMATION FOR SEQ ID NO:18:

(i) SEQUENCE CHARACTERISTICS:
            (A) LENGTH: 29 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:18:

AAGCTTCAGG GAGAAGTGAA ATGACAACC                                                 29

(2) INFORMATION FOR SEQ ID NO:19:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:19:

GTCTGAGTCT GAGTCAAGCT TCAGGGAGAA                                                30

(2) INFORMATION FOR SEQ ID NO:20:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:20:

CTCGAGCAGA CCTAAAACAC AATAGAGAGT TCC                                            33

(2) INFORMATION FOR SEQ ID NO:21:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:21:

```
GTCTGAGTCT GAGTCCTCGA GCAGACCTAA                                    30

(2) INFORMATION FOR SEQ ID NO:22:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:22:

AAGCTTCTGT AGAGTTAAAA AATGAACCCC ACGG                                34

(2) INFORMATION FOR SEQ ID NO:23:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:23:

GTCTGAGTCT GAGTCAAGCT TCTGTAGAGT                                    30

(2) INFORMATION FOR SEQ ID NO:24:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:24:

CTCGAGCCAT TCATTTTTC TACAGGACAG CATC                                34

(2) INFORMATION FOR SEQ ID NO:25:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:25:

GTCTGAGTCT GAGTCCTCGA GCCATTTCAT                                    30

(2) INFORMATION FOR SEQ ID NO:26:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:26:

GTCTGAGTCT GAGTCAAGCT TAACAAGATG GATTATCAA                          39
```

-continued (2) INFORMATION FOR SEQ ID NO:27:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:27:

GTCTGAGTCT GAGTCCTCGA GTCCGTGTCA CAAGCCCAC       39